United States Patent
Muir et al.

(10) Patent No.: US 6,251,660 B1
(45) Date of Patent: Jun. 26, 2001

(54) DEVICES AND METHODS FOR DETECTING TARGET MOLECULES IN BIOLOGICAL SAMPLES

(75) Inventors: Andrew R. Muir, Cohasset; T. Christian Boles, Waltham; Christopher P. Adams, Somerville, all of MA (US)

(73) Assignee: Mosaic Technologies, Inc., Waltham, MA (US)

(*) Notice: Subject to any disclaimer, the term of this patent is extended or adjusted under 35 U.S.C. 154(b) by 0 days.

(21) Appl. No.: 09/200,126

(22) Filed: Nov. 25, 1998

Related U.S. Application Data

(60) Provisional application No. 60/066,508, filed on Nov. 25, 1997.

(51) Int. Cl.[7] .............................. C12M 1/34; B01D 11/04
(52) U.S. Cl. ....................... 435/287.2; 422/236; 422/258; 422/272
(58) Field of Search .................. 435/6, 7.1, 7.2, 435/183, 91.1, 91.2, 257.2, 287.2; 436/501, 94, 800; 204/456; 530/350, 387.1; 536/23.1, 24.3, 24.33; 422/99, 100, 113, 142, 189, 197, 236, 242, 258, 272

(56) References Cited

U.S. PATENT DOCUMENTS

| | | |
|---|---|---|
| 3,217,710 | 11/1965 | Beall et al. . |
| 4,766,064 | 8/1988 | Williams et al. ........................ 435/6 |
| 4,829,098 | 5/1989 | Hoffman et al. ........................ 522/5 |
| 5,034,428 | 7/1991 | Hoffman et al. ........................ 522/5 |
| 5,188,615 | * 2/1993 | Haber et al. ........................... 604/203 |
| 5,310,650 | 5/1994 | McMahon et al. ...................... 435/6 |
| 5,482,836 | 1/1996 | Cantor et al. ............................ 435/6 |
| 5,494,810 | 2/1996 | Barany et al. ....................... 435/91.52 |
| 5,587,128 | 12/1996 | Wilding et al. ......................... 422/50 |
| 5,589,136 | 12/1996 | Northrup et al. ..................... 422/102 |
| 5,591,573 | 1/1997 | Whalen et al. . |
| 5,610,287 | 3/1997 | Nikiforov et al. ................... 536/24.3 |
| 5,639,423 | 6/1997 | Northrup et al. ....................... 122/50 |
| 5,641,658 | 6/1997 | Adams et al. ........................ 435/91.2 |
| 5,646,039 | 7/1997 | Northrup et al. ................. 435/287.2 |
| 5,674,742 | 10/1997 | Northrup et al. ................. 435/286.5 |
| 5,679,524 | 10/1997 | Nikiforov et al. ........................ 435/6 |
| 5,741,639 | 4/1998 | Ensing et al. ............................ 435/6 |
| 5,762,876 | 6/1998 | Lincoln et al. ......................... 422/67 |
| 5,830,711 | 11/1998 | Barany et al. ....................... 435/91.1 |

FOREIGN PATENT DOCUMENTS

| | | |
|---|---|---|
| 94 17 612 | 1/1995 | (DE) . |
| 0 397 424 | 11/1990 | (EP) . |
| 0 671 626 A1 | 3/1994 | (EP) . |
| WO 86 00704 | 1/1986 | (WO) . |
| WO90/0758 | 7/1990 | (WO) . |
| WO 95 15681 | 6/1995 | (WO) . |
| WO96/04404 | 2/1996 | (WO) . |
| WO97/41256 | 11/1997 | (WO) . |
| WO 97 47967 | 12/1997 | (WO) . |
| WO97/45554 | 12/1997 | (WO) . |

OTHER PUBLICATIONS

Abrams et al., Diagnostic Gene Detection & Quantification Technologies for Infectious Agents & Human Genetic Diseases, IBC Library Series Publication #948, International Business Communications, Inc., Southborough, Massachusetts, 171–189 (1997).

(List continued on next page.)

Primary Examiner—Bradley L. Sisson
(74) Attorney, Agent, or Firm—Hamilton, Brook, Smith & Reynolds, P.C.

(57) ABSTRACT

Devices and methods for detecting the presence, or absence of the presence of at least one target molecule employing a receptacle housing a reaction chamber comprised of at least one compartment containing suitable reagents for the detection of the target molecule are disclosed.

35 Claims, 14 Drawing Sheets

OTHER PUBLICATIONS

Barany et al., "Genetic Disease Detection and DNA Amplification Using Cloned Thermostable Lega", *Proc. Natl. Acad. Sci. 88*:189–193 (1991).

Biagioni et al., "A New Method for the Preparation of DNA–Cellulose", *Analytical Biochemistry 89*:6160618 (1978).

Bing et al., "Bridge Amplification: A Solid Phase PCR system for the Amplification and Detection of Allelic Differences in Single Copy Genes", Seventh International Symposium on Human Identification, Promega Corporation, Madison, Wisconsin (1996).

Burns et al., "An Integrated Nanoliter DNA Analysis Device" *Science 282*:484–487 (1998).

Jarrett, H.W., "Affinity Chromatography with Nucleic Acid Polymers", *J. Chromatogr. 618*:315–339 (1993).

Joyce, G.F., "Amplification, Mutation and Selection of Catalytic DNA", *Gene 82*:83–87 (1989).

Kopp et al., "Chemical Amplification: Continuous–Flow PCR on a Chip", *Science 280*:1046–1048 (1998).

Mergny et al., "Fluorescence Energy Transfer as a Probe for Nucleic Acid Structures and Sequences", *Nucleic Acids Research 22*(6):920–928 (1994).

Ness et al., "A Versatile Solid Support System for Oligodeoxynucleotide Probe–Based Hybridization Assays", *Nucleic Acids Research 19*(12):3345–3350 (1991).

Nielsen et al., "Sequence–Selective Recognition of DNA by Strand Displacement with a Thymine–Substituted Polyamide", *Science 254*:1497–1500 (1991).

Saiki et al., "Primer–Directed Enzymatic Amplification of DNA with a Thermostable DNA Polymerase", *Science 239*:487–491 (1988).

Smith et al., "Covalent Binding of Proteins and Glucose–6–Phosphate Dehydrogenase to Cellulosic Carriers Activated with s–Triazine Trichloride", *Analytical Biochemistry 61*:392–415 (1974).

Timofeev et al., "Regioselective Immobilization of Short Oligonucleotides to Acrylic Copolymer Gels", *Nucleic Acids Research 24*(16):3142–3148 (1996).

Tsurui et al., "A Rapid and Efficient Cloning Method with a solid–Phase DNA Probe: Application for Cloning the 5'–Flanking Region of the Gene Encoding Human Fibronectin", *Gene 88*:233–239 (1990).

Tyagi et al., "Molecular Beacons: Probes that Fluoresce upon Hybridization", *Nature Biotechnology 14*:303–308 (1996).

Zebala et al., PCR Strategies, "Detection of Leber's Hereditary Optic Neuropathy by Nonradioactive Ligase Chain Reaction", Academic Press, Boston, Massachusetts, 335–346 (1995).

* cited by examiner

DEVICES AND METHODS FOR DETECTING TARGET MOLECULES IN BIOLOGICAL SAMPLES

RELATED APPLICATION

This application is claiming priority to Provisional application No. 60/066,508, filed on Nov. 25, 1997. The entire teachings of which are incorporated herein by reference.

BACKGROUND OF THE INVENTION

The screening of a biological sample for contaminants plays a vital role especially in the area of clinical medicine . The potential contaminants include infectious bacteria, disease causing viruses and parasites that can seriously compromise the health of a mammal, and even lead to death. It is important to screen for such pathogens in order to prevent the transmission of such diseases as caused by these contaminants. For example, it is critical to evaluate blood that was obtained from a donor prior to a transfusion into a recipient. This evaluation consists of screening the blood for the presence of any pathogen. Typically, this evaluation is performed in a laboratory well equipped for such a task. However, in certain milieus, the presence of a sophisticated laboratory is not a realistic expectation.

The screening of a biological sample is not limited to examining whether or not the sample is contaminated. Screening a biological sample is often done diagnostically, looking for the presence, or absence, of certain indicating biomolecules. An example of this scenario is when the blood is analyzed for the presence of certain lactate dehydrogenase isozymes which are particular to the heart. If these isozymes are present in the blood, this is indicative of a myocardial infarction. Also, testing is conducted looking for the presence, or absence, of genetic markers whether as expressed proteins (for example, MHC antigens) or in the genome. Again, these types of tests are usually performed in technically sophisticated laboratories.

A need exists for the ability to conduct screening of biological samples in environments that are not generally associated with technically sophisticated laboratories.

SUMMARY OF THE INVENTION

The present invention pertains to novel devices and methods for screening a biological sample for the presence, or absence, of at least one target molecule. The presence of a predetermined target molecule can be used to indicate bacterial, viral, fungi and/or parasitic contamination of the sample. Additionally, the presence of a predetermined target molecule can also be used to indicate specific biomolecules in the sample which are endogenous to the host from which the sample was obtained.

This target molecule can be a nucleic acid, DNA or RNA (single or double stranded), polypeptide, protein, and combinations thereof. The invention encompasses the screening of one particular target molecule or a heterogenous group of target molecules present in the biological sample. The methods described herein provide for a relatively fast qualitative assay to determine the presence of contaminating organisms or endogenous biomolecules within a biological sample.

The present invention pertains to a devices that can be used for the analysis of molecules or substances present in biological material such as bodily fluids (e.g., blood, urine, saliva, cerebral spinal fluid, etc). The instant invention also pertains to apparatuses for operating the devices of the present invention, including those that cause motion of liquid reagents and perform detection of sample components. The invention also pertains to methods for using the devices and apparatuses of the instant invention for analysis of a biological sample. The devices of the present invention can be used in a variety of embodiments.

In one embodiment, the invention pertains to a device for testing a biological sample comprising a receptacle housing at least one reaction chamber comprising at least one compartment. More specifically, the test device comprises a receptacle which is attached to at least one sample collection unit housing bodily fluid. This bodily fluid serves as the biological sample which can undergo analysis for detecting the presence of at least one target molecule.

In one embodiment, the invention pertains to a breakable compartment. The barrier that partitions one compartment from the adjacent compartment can comprise breakable material. If the barrier is ruptured between two adjacent compartments, then the contents of each will be allowed to mix. The breakable barriers can be caused to break by applying an appropriate pressure against the barrier such that the breakable barrier rupture (for example, using an apparatus described herein). A physical object applied against the breakable barrier can cause it to rupture. An instrument with a sharp end which is applied against the breakable barrier can also cause it to rupture.

In one embodiment, the invention pertains to a device for testing a biological sample comprising a receptacle housing at least one reaction chamber comprising at least one compartment, wherein the compartment(s) comprises at least one bacterial vital staining reagent In this embodiment, the invention pertains to a device and method for testing a biological sample for the presence of bacteria. The bacterial cells of the biological sample are subjected to staining using vital bacterial stains that can detect a specific genius and/or species of bacteria.

In one embodiment, the invention pertains to a device and method for testing a biological sample comprising a receptacle housing at least one reaction chamber wherein said chamber comprises breakable compartments, wherein one compartment comprises at least one cell lysing reagent, another compartment comprises at least one reagent for the inactivation of amplification inhibitors, another compartment comprises at least one reagent for nucleic acid amplification and another compartment comprises at least one reagent for labeling at least one target molecule, wherein the labeled target molecule is subject to a method of detection.

In another embodiment, the invention pertains to a device for testing a biological sample comprising a receptacle housing at least one reaction chamber wherein said chamber comprises breakable compartments, wherein one compartment comprises at least one cell lysing reagent and another compartment comprising at least one reagent for labeling at least one target molecule, wherein the labeled target molecule is a polypeptide or protein subject to a method of detection. Typically, the method of detection is with a detectably-labeled antibody, or antibody fragment, that is specific for the target polypeptide or protein.

Thus, as a result of the work described herein, devices are now available for fast, efficient and easy to use methods of screening biological samples for the presence of pathogens or any other biomolecules.

DETAILED DESCRIPTION OF THE INVENTION

The present invention pertains to novel devices and methods for screening a biological sample for the presence, or absence, of at least one target molecule. The presence of a target molecule can be used to indicate a microbiological pathogen such as a bacteria, virus, fungi or parasite present in the sample. Additionally, the presence, or absence, of a target molecule can also be used to indicate specific biomolecules in the sample which are endogenous to the host from which the sample was obtained. This target molecule can be a nucleic acid molecule, polynucleotide, DNA or RNA (single or double stranded), polypeptide, protein, and combinations thereof. The invention encompasses the screening of one particular target molecule or a heterogenous group of target molecules present in the biological sample. The methods described herein provide for a fast assay to determine the presence, or absence, of contaminating organisms or endogenous biomolecules within a biological sample.

In one embodiment, the invention pertains to a device for testing a biological sample comprising a receptacle housing at least one reaction chamber comprising at least one compartment.

Figure 2:
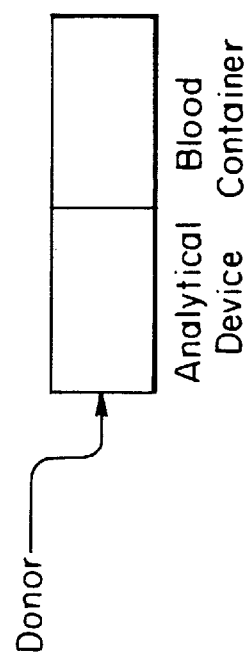
FIG. 2 depicts the device of the invention as part of the sample collection unit.
Figure 1:
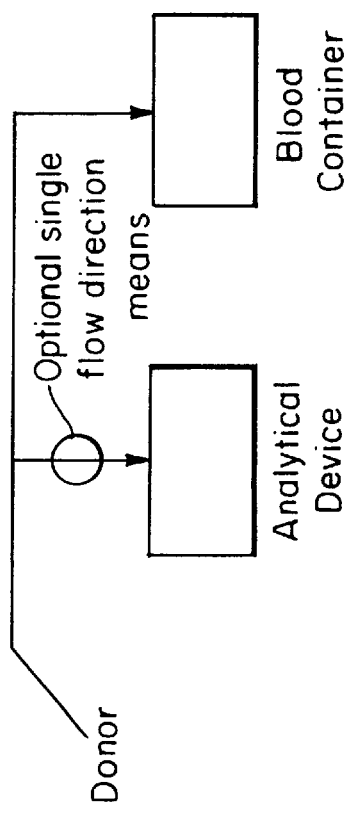
FIG. 1 depicts the device of the invention positioned such that the sample for analysis taken from a donor can be screened prior to depositing the sample in a sample collection unit.
Figure 3:
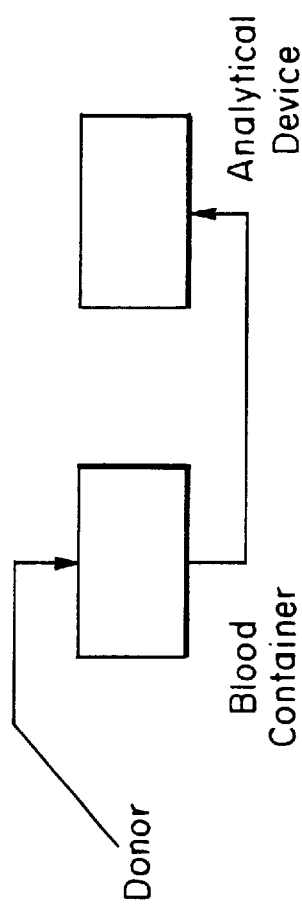
FIG. 3 depicts the device of the invention placed after the sample collection unit which houses the biological sample taken from a donor.

The device in this embodiment is attached to at least one sample collection unit (e.g., for the collection of blood or urine) and to at least one subject. (See FIGS. 1, 2, 3). Any attachment of this embodiment comprises a biocompatible material. In one embodiment, the subject is a donor of blood. In another embodiment, the subject is a blood transfusion recipient. In still another embodiment, the device of the present invention is attached to the withdrawing needle employed to extract blood from a donor and attached simultaneously to a sample collection unit capable of housing blood. In another embodiment, the sample collection unit houses blood that is to be used for a blood transfusion, wherein the sample collection unit is attached along with the transfusion recipient to the device of the instant invention. A sample of either the sample collection unit of blood or blood taken directly from a donor comprise the biological sample and are placed into the device and can be subjected to analysis. Preferably, the inner surface of the sample collection unit comprises biocompatible material.

The biological sample can be a bodily fluid. The bodily fluid can include, but is not limited to, blood, urine, tracheal exudate, saliva, cerebral spinal fluid, aqueous humor, vitreous humor, semen and tissue homogenate. The biological sample can contain endogenous biomolecules, for example, isozymes like lactate dehydrogenases used for diagnosing certain illnesses such as myocardial infarctions. The biological sample can be contaminated with at least one bacteria, virus, fungi, parasite or combinations thereof. Bacterial contamination of the biological sample can include, but not are limited to, Gram-positive, Gram-negative, Staphylococcus, Streptococcus, Neisseria, Corynebacterium, Hemophilus, Bordetella, Brucella, Pasteurella, Escherichia, Salmonella, Shigella, Bacteroides, Rickettsia, Chlamydiae Spirochetes and Mycobacteria. A virus, or virus particle, can also contaminate the biological sample and can include, but is not limited to, DNA viruses, RNA viruses, Picornovirus, Reovirus, Togavirus, Arenavirus, Bunyavirus, Rhabdovirus, Orthomyxovirus, Paramyxovirus, Coronavirus, Adenovirus, Herpesvirus, Poxvirus, Hepatitis, Papovavirus and Parvovirus.

Parasites are also to be considered as potential contaminants of the biological sample and can include, but are not limited to, Protozoa such as Sarcodina, Mastigophora, Sporozoa, Amoebae, Giardia, Trichomonas; also, Trypanosome, Leishmania, Plasmodium, Pneumocystis, Toxoplasma, Ascaris, Enterobius, Trichinella and Trematoda.

Fungi are also to be considered as potential contaminates of the bioogical sample and can include, but are not limited to, Histoplasma capsulatum, Coccidiodes immitis, Blastomyces dermatitidis, Paracoccidioides brasiliensis, Cryptococcus neoforms, Candida, Aspergillus, Rhizopus, Absidia, Mucor, Saksenaea and Cunninghamella.

The device of the present invention comprises a receptacle. The receptacle comprises a reaction chamber. The receptacle can be comprised of durable material such as, stainless steel, plastic, brass, ceramic, glass or silica. The inner surface of the receptacle can be comprised of material that is heat resistant such as heat resistant stainless steel, plastic, brass, ceramic, glass or silica. This receptacle allows for the reaction chamber to be completely sequestered within it. In one embodiment, the receptacle can sequester completely, or near completely (from about 85% to about 95%), the reaction chamber allowing for at least one orifice. In another embodiment, the receptacle has at least two orifices, for example, an entry orifice and an exist orifice.

The reaction chamber of the device comprises at least one compartment. The reaction chamber can be comprised of a biocompatible material. The biocompatible material can include, but is not limited to, nylon, polyurethane, polethylene terphthalate, polypropylene, derivatives and combinations thereof. Preferably, the reaction chamber comprises biocompatible material that is resistant to temperature fluctuations (approximately from about −10° C. to about 110° C.). In one embodiment, the reaction chamber has at least one orifice. In another embodiment, the reaction chamber has at least two orifices. Preferably, the orifice(s) of the reaction chamber align with the orifice(s) of the receptacle.

In one embodiment, there is at least one compartment residing within the reaction chamber. In a preferred embodiment, the outer surface of the compartments) is apposite to the inner surface of the reaction chamber. In a more preferred embodiment, the outer surface of the compartment(s) is contiguous with the inner surface of the reaction chamber. The compartment can be comprised of biocompatible material. The biocompatible material can be affixed (e.g., coated) with at least one reagent. In one embodiment, the biocompatible material is silica which provides functional groups from which reagents can be attached. Preferably, a solution carrying the biological sample can move through the compartment from which reagents are attached and can interact with components of the sample. In a preferred embodiment, the interior surface of the compartment(s) exposed to the lumen of the compartments) comprises a biocompatible material. In another embodiment, there are at least two compartments within the reaction chamber. Where there are two or more compartments within the reaction chamber, the compartments are separated from each other by a barrier. Preferably, this barrier is comprised of a biocompatible material. In one embodiment, the barrier separating the compartments is impermeable to any ion or molecule in either the liquid or gas phase. This impermeable barrier can comprise biocompatible material which restricts the passage of molecules from one compartment into the adjacent compartment. For example, the size restriction can include molecules having a molecular mass above 150 Daltons; a polypeptide having a molecular mass of 2 kilodaltons will be restricted and not allowed to pass into the adjacent compartment. In another embodiment, the barrier is a semipermeable membrane. Preferably, the semipermeable membrane selects against molecules having a molecular size greater than 100 kilodaltons. In a more preferred embodiment, the membrane selects against molecules having a molecular size greater than 300 daltons.

In one embodiment, the barriers separating the individual compartments within the reaction chamber are breakable. When the appropriate pressure (e.g., pressure sufficient to break the barrier) is applied to a given barrier, then that barrier will rupture allowing the contents of one compartment to enter into the adjacent compartment, thus introducing the contents into the compartments. In one embodiment, the compartment(s) has a first end and a second end. Preferably, the first end comprises an entry orifice and the second end comprises an exit orifice. In another embodiment, the first end contains an entry orifice and the second end lacks any type of orifice. In one embodiment, the first end can be used to introduce liquid reagent into the compartment, while the second end can be used to allow passage of reagent and/or sample into an adjacent compartment. In a preferred embodiment, the orifices of the receptacle, reaction chamber, and compartment(s) align so as to allow transmission of material, for example fluid, from the receptacle through the reaction chamber and into the compartment(s). Entry of the biological sample from an external source, such as a connected sample collection unit, or one that is not connected, can be accomplished by means well known to the art such as valve switching in the case of an attached sample collection unit, or syringe emptying in the case of an unattached source. The compartment(s) can be comprised of a pliable or non-pliable biocompatible material. In a preferred embodiment, the compartment(s) is comprised of a pliable biocompatible material.

Figure 4:
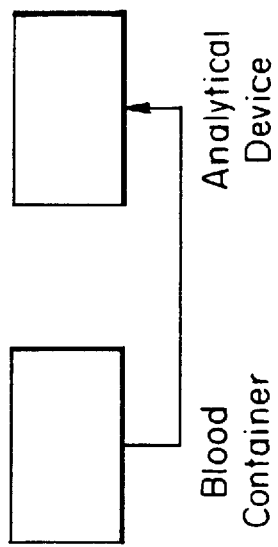
FIG. 4 depicts the device of the invention in direct contact with the sample collection unit.

The device of the present invention can, for example, be connected to a blood donor via a connecting tube leading from a withdrawing needle, thereby allowing for screening of pathogenic contaminants immediately after blood withdrawal. (See, FIGS. 1 and 2). The device of the invention can, for example, be connected to a sample containing unit comprising bodily fluid. (See, FIG. 4). The bodily fluid can be analyzed for pathogenic contaminants.

Cells contained within a biological sample can be lysed with at least one cell lysing reagent. Preferably, this lysing step occurs within one compartment residing within the reaction chamber. This lysing step will liberate cellular components, including nucleic acids, polypeptides, proteins and cellular debris, that were once constrained by the cell membrane. The target molecule can be a polynucleotide sequence which is contained in a nucleic acid molecule. The target molecule can be a polypeptide and protein. The biological sample can be contaminated with a pathogen, for example, a bacteria, virus, parasite or fungi in which the pathogen itself is subjected to lysis, thereby liberating its genomic material, or the pathogen can be of a type which invades and incorporates genetic material within a host cell. When the host cell, which can be part of a biological sample, is lysed, the host cell's genomic material is released along with the pathogen's incorporated genetic material. For example, some viruses, such as retroviruses, incorporate their genetic material into the host's genome. Also, some viruses will assemble into mature virus particles inside the host cell. Once the host cell is lysed, then the viral genetic material will be liberated. This will generally be true even if the virus had formed its viral coat within the host's cell. Preferably, the lysing reagent can lyse the viral coat, thereby liberating the viral genome.

The cell lysing reagent can include, but is not limited to, alkali, detergents, hypotonic solution and combinations thereof. The lysing reagent can be in the form of a powder, to which liquid is added to form a solution, or in a solution form. Those skilled in the art will be familiar with a suitable cell lysing reagents and protocols. In one embodiment, the biological sample is contacted with alkali, thereby rupturing the cell membrane and releasing cellular contents. In another embodiment, the biological sample is contacted with at least one detergent such as Triton® (Union Carbide, Danbury, Conn.), Tween® (ICI,UK), sodium laural sulfate (specifically, SDS or Laureth 12), NP-40, and combinations thereof. For example, the biological sample is placed in a solution comprising from about 1% to about 5% Laureth 12 with from about 0.5% to about 2% tween (for example, Tween® (ICI,UK) 20). In still another embodiment, the cells are placed in a lysis compartment that contains a hypotonic solution, for example, 10 mM Tris and 10 mM EDTA. This solution will have a low solute concentration and therefore there will be a net movement of water into the cells, causing them to swell and rupture. Generally, gentle mixing will accompany any of these lysing protocols to ensure complete cell lysis. This can be accomplished by a rocking motion, agitation, vortex-mixing or other mechanical modes of mixing.

The target molecule can be a polynucleotide. In one embodiment, a nucleic acid probe can be used to detect the target polynucleotide. Preferably, the nucleic acid probe comprises a sequence that is at least partially complementary to the target polynucleotide. Under suitable conditions for hybridization, the target polynucleotide is placed in contact with the nucleic acid probe such that there is a hybridization complex formed. However, the target polynucleotide may first need to be amplified.

There can be a homogeneous or heterogenous group of target polynucleotide sequences both in terms of organismal origin and biochemical classification of biomolecules. The target molecule can originate from a pathogen or it can be an endogenous biomolecule, such as a metabolic enzyme normally functioning within a human. If there are a heterogenous group of target polynucleotide sequences, then they can originate from one pathogen (having different target nucleotide sequences) or from a group of different pathogens or a combination thereof. The target polynucleotide sequence may be difficult to detect due to the scarcity of its presence within the biological sample at the time of analysis. In order to facilitate detection of the target polynucleotide sequence, amplification can be performed.

The cell lysate can then be subjected to at least one reagent that will inactivate nucleic acid amplification inhibitors. The reagent can include, but is not limited to, diethylpyrocarbonate (hereinafter "DEP"), proteases such as proteinase K, and combinations thereof. The reagent can be in the form of a powder, to which liquid is added to form a solution, or already in a solution form. Proteinase K is a very good protease for digesting nuclei to release DNA or RNA into a form accessible to polymerases. The cell lysate can be contacted with from about 80 µg/mL to about 120 µg/mL of Proteinase K. Lysis of cells in the presence of DEP prevents the degradation of DNA and RNA by nucleases. The lysate can be contacted with from about 0.01% to about 0.05% DEP. These techniques are well known to those skilled in the art. (See, PCR Protocol, Innis, M. A., et al. (eds.), Academic Press, Inc., San Diego, Calif., (1990); the entire teachings of which are incorporated herein by reference).

A variety of methods for amplification can be applied to the target polynucleotide sequence. These methods include, but are not limited to Polymerase Chain Reaction (PCR), Ligase Chain Reaction (LCR), Cascade and Bridge amplification. (See for LCR: U.S. Pat. Nos. 5,494,810 and 5,830,711 both to Barany, F., et al.; Barany, F. et al., *PNAS, USA*, 88:189–193 (1991); for Cascade: U.S. Ser. No. 60/064,166; for Bridge: U.S. Pat. No. 5,641,658 to Adams and Krom; the entire teachings of which are incorporated herein by reference).

In one embodiment, at least one target polynucleotide is subjected to PCR amplification. For PCR amplification, predetermined primers are applied to the target polynucleotide sequence(s) under conditions suitable to facilitate hybridization between the primers and target polynucleotide sequence(s). The primers of the current invention can be selected based upon known nucleotide sequences of pathogens or endogenous biomolecules of interest. Primers are selected, or synthesized, based on their ability to hybridize to portions of the target polynucleotide in such a manner as to facilitate DNA Polymerase synthesis. Such conditions are well known to those skilled in the art. (See, Ausubel, F. M., et al. (eds.), *Current Protocols in Molecular Biology*, Greene Publishing Associates and Wiley-Interscience, $5^{th}$ ed., (1991), vol. 2, pp. 15.1.1–15.4.6; Saiki, R. K., et al., *Science*, vol. 239, pp. 487–491 (1988); the entire teachings of which are incorporated by reference herein).

A thermocycler can be housed within the receptacle or attached to the receptacle using biocompatible material. The thermocycler can be attached or contained within a compartment within the reaction chamber. Preferably, the entity housing the thermocycler comprises heat stable materials. There have recently been developments in the art where small reliable thermocyclers are commercially available, for example, from Cepheid. (See U.S. Pat. Nos. 5,587,128; 5,639,423; 5,646,039; 5,674,742; 5,589,136; Burns et al., *Science*, 282:484–487 (1998); Kopp et al., *Science*, 280:1046–1048 (1998); the entire teachings of which are incorporated herein by reference). Additionally, a chamber or a compartment could be coated with a resistive layer and fitted with an electric thermometer such as a thermistor or platinum-resistant thermometer which could provide an even smaller and simpler thermocycler. In one embodiment, the thermocycler is contained within the receptacle attached via biocompatible material to a compartment containing at least one target polynucleotide sequence annealed to appropriate primers. In another embodiment, the thermocycler is external to the device of the present invention and is attached via biocompatible material to said device or the device is detached from the sample collection unit.

In another embodiment, the invention pertains to the amplification of at least one target polynucleotide molecule on a support surface. (See, U.S. Pat. No. 5,641,658; U.S Ser. No. 08/800,840; the entire teachings of which are incorporated by reference herein). Preferably, the target polynucleotide is double stranded and has a first and a second target polynucleotide sequence. This method comprises forming a hybridization product comprising at least one first target polynucleotide sequence, at least one second polynucleotide and at least one support. Preferably, the support is epoxy silane derivatized silica. More preferably, the support is a plastic material. The support can be a filter, fiber, membrane, bead, dipstick, rod and the like. The support contains the second polynucleotide sequence comprising a complementary sequence to the target sequence. Preferably, the second polynucleotide is covalently bound to the support. Preferably, the second polynucleotide is covalently bonded to a polyacrylamide layer that which is covalently bonded to the support. (See, U.S. Ser. No. 08/812,105 now U.S. Pat. No. 6,060,288). At least one first target polynucleotide sequence is placed in contact with the second polynucleotide sequence under conditions suitable for hybridization. The second polynucleotide serves as a primer for amplifying the first target polynucleotide sequence. A first amplification product is formed comprising a polynucleotide sequence complementary to the target polynucleotide covalently extending from the second polynucleotide. Preferably, the target polynucleotide amplification product is single stranded and comprises complementary sequences to both the first and second target polynucleotide sequences. The amplification product's complementary second target polynucleotide sequence comprises a complementary sequence to a third polynucleotide.

Preferably, the support contains the third polynucleotide sequence. Preferably, the third polynucleotide is covalently bound to the support. The first target polynucleotide sequence is released from hybridization with the second polynucleotide under conditions suitable for denaturation. The release of this first target polynucleotide sequence will result in the release of the target polynucleotide, thereby allowing the target polynucleotide to participate in further hybridization reactions.

A second hybridization is performed comprising the first amplification product and the third polynucleotide and a further second polynucleotide placed in contact with one another under conditions suitable for hybridization. Preferably, the third polynucleotide is covalently bound to the support. The third polynucleotide can form a second hybridization product with the first amplification product. The formation of this second hybridization product allows for the formation of a second amplification product comprising a polynucleotide complementary to the first amplification product covalently extending from the third polynucleotide. Thus, the target polynucleotide and the first and second amplification products are capable of multiple hybridization and amplification reactions. Bridge amplification of the target polynucleotide molecule. Bridge amplification can be performed on a variety of solid surfaces, including glass or plastic beads, glass fibers, plastic dipsticks, glass slides, plastic or glass tubes, multi-well plates, and micromachined silicon wafers or glass substrates, etc.

A pair of predetermined polynucleotide primers is covalently attached to a surface. These primers are relatively short length, from about 15 to about 50 nucleotides in length, of single stranded DNA. The sequence of each primer is complementary to the base sequence at one end of the target polynucleotide to be amplified. One such primer is prepared to be complementary to one strand of the target polynucleotide, whereas the other is complementary to the opposite strand of the target polynucleotide. Both primers can have their 5' ends attached to a surface, leaving their 3' ends free to participate in the PCR reaction. The surface density of primers is sufficient for the amplified product from the Bridge reaction to span between primer anchorages in the form of a double stranded polynucleotide bridge.

The present invention encompasses nucleic acids being covalently immobilized to a surface. This surface can include an electrophoretic medium. Suitable matrices include acrylamide and agarose. However, other materials can be used. Examples include chemically modified acrylamides, starch, dextrans, cellulose-based polymers. The nucleic acids designed to be immobilized within the gel medium can be modified by attaching an acrylamide moiety to, for example, the 5' end of the nucleic acid. In preparing the electrophoresis medium, for example, acrylamide, the modified nucleic acid molecules are added to the acrylamide preparation and allowed to polymerize. This will embed the modified nucleic acid molecules within the gel. These modified nucleic acids can be, for example, a probe used to detect a target polynucleotide within a biological sample, or primers that can be used to amplify the target polynucleotide. (See, U.S. Ser. No. 08/971,845; the entire teachings of which are incorporated herein by reference).

This technology can be used for the current invention. The surface of the lumen of the amplification compartment, or detection compartment, for example, can be coated with a medium, such as acrylamide, that has incorporated nucleic acid molecules. These nucleic acids can be used, for example, amplification or detection. The biological sample containing the target polynucleotide can be passed through a compartment comprising immobilizing nucleic acid molecules, thereby facilitating, for example, amplification or detection.

Preferably, the surface with primers attached is immersed in a compartment containing all the reagents necessary for a PCR reaction. (See, Ausubel, F. M., et al. (eds.), *Current Protocols in Molecular Biology*, Greene Publishing Associates and Wiley-Interscience, $5^{th}$ ed., (1991), vol. 2, pp. 15.1.1–15.4.6; Saiki, R. K., et al., *Science*, vol. 239, pp. 487–491 (1988)). With each repetitive cycle, the quantity of surface bound amplificate will be increased, and additional free target polynucleotide molecules will bind and enter the process. With repetitive cycling of this reaction, the quantity of amplified product increases approximately exponentially, until the primers become saturated or other reaction components become exhausted.

The present invention pertains to a method for detecting a target polynucleotide sequence in a polynucleotide molecule within a biological sample using an immobilized probe comprising multiple sequential polynucleotide displacement for signal amplification.

An immobilized probe complex is formed by contacting a first polynucleotide sequence with a second polynucleotide sequence under conditions suitable for hybridization between the first and second polynucleotide sequence. (See U.S. Ser. Nos. 08/971,845; 06/046,708 60/046,708, now U.S. Ser. No. 08/971,845; and 08/812,105 now U.S. Pat. No. 5,932,711 ; 09/188,086 the entire teachings of which are incorporated by reference). The first polynucleotide sequence is immobilized to a first surface. The surface of the present invention can be a surface on a solid support, such as, gels (like, polyacrylamide, starch or agarose), glass, plastic and wax-based.

The means of attachment of a nucleic acid to a surface, such as a solid support surface, can be by simple adsorption. Preferably, the attachment is mediated through a covalent bond between the nucleic acid and some chemical moiety associated with the surface, for example, an amine or carboxyl group, or acrylamide bound to any region of the nucleic acid. Chemical crosslinkers can be employed to immobilize a nucleic acid to a surface. An example of such a chemical crosslinker is carbodiimide (such as, 1-ethy-3, 3-dimethylaminopropylcarbodiimide) which can be used to link the phosphate group on the 5' end of a nucleic acid with amine group on the surface. Additionally, ionic interactions can also facilitate such immobilization of the nucleic acid. The binding can be direct as between the nucleic acid and surface, or indirect such that an intermediate molecule lies between the nucleic acid and the surface. This intermediate molecule need not have any precise length.

Affinity reagents can also be employed as a means to immobilize a nucleic acid to a surface. For example, a nucleic acid carrying avidin or biotin moieties to a surface containing biotin or avidin moieties, respectively, will bind the nucleic acid to the surface. Another example of using an affinity-based immobilization technique is to coextensively link the nucleic acid of interest to an affinity ligand, again avidin or biotin provide useful examples. The cognate receptor to the ligand, for example, if biotin is the ligand, then avidin will be the cognate receptor, will have attached to it a magnetic particle. When a magnetic field is applied to the surface, the magnetic particle, along with that which attached to it, will be immobilized to the surface.

A displacement complex is formed by contacting the immobilized probe complex with a target third polynucleotide sequence under conditions suitable for the target polynucleotide sequence to displace at least one second polynucleotide sequence from the immobilized complex, and hybridize the target polynucleotide sequence with its cognate first polynucleotide sequence of the complex. Preferably, the first polynucleotide sequence has a higher affinity for the target third polynucleotide sequence than for the second polynucleotide sequence.

At least one displaced second polynucleotide sequence is transferred from the first immobilizing surface to a second immobilizing surface. The phase containing the displaced second polynucleotide sequence (or any displaced polynucleotide sequence), for example, a liquid phase, can be separated from an immobilized complex by processes such as chromatography, filtration, centrifugation, decantation or pipetting, for example. Additionally, transfer can be accomplished by counter current distribution, gravitational flow, electrically induced endosmotic flow, wetting, capillary action, pump-mediated flow and electrophoresis.

A second immobilized probe complex is formed by contacting a fourth polynucleotide sequence with a fifth polynucleotide sequence under conditions suitable for hybridization between the fourth and fifth polynucleotide sequences. The fourth polynucleotide sequence is immobilized to a second surface.

A second immobilized displacement complex is formed. The immobilized second probe complex is contacted with the transferred second polynucleotide sequence that was displaced during the first displacement complex event, under conditions suitable for the second polynucleotide sequence to displace at least one fifth polynucleotide sequence and hybridize to its cognate fourth polynucleotide sequence. Preferably, the fourth polynucleotide sequence has a higher affinity for the second polynucleotide sequence than for its fifth polynucleotide sequence complex partner. This second displacement complex event generates a fifth polynucleotide sequence that can be transferred to a subsequent surface or be used to generate a signal for detection.

A third immobilized probe complex is formed by contacting the fifth polynucleotide sequence with an immobilized beacon probe, wherein the probe has a complementary sequence to the fifth polynucleotide sequence, under conditions suitable for hybridization between the fifth polynucleotide sequence and the beacon probe. The beacon probe is immobilized to a third surface. The beacon probe has sequences which are complementary such that it will form a secondary structure with itself. Due to this secondary structure, the fluorophore and quencher are brought into proximity with one another such that the fluorescent signal is quenched. When the fifth polynucleotide sequence hybridizes to the beacon probe, the fluorophore and quencher are spread apart from one another, thereby producing a fluorescent signal.

The cycle of probe and displacement complex formation followed by the transfer of the displaced polynucleotide sequence can be repeated with the result of amplifying the assay signal. Multiple cycles can involve multiple surfaces. These surfaces can be coextensive or spatially apart from one another, for example, two 50 mL conical tubes as representing two surfaces spatially apart. If the surfaces are coextensive they can be separated by partitions, for example, a size-selective permeable membrane which can separate coextensive surfaces allowing for only the movement of a displaced polynucleotide sequence containing molecule while retention of a complex (presumably not immobilized) in a particular surface is accomplished.

This embodiment also embraces a solid support matrix wherein there are multiple reaction stations spatially aligned throughout the matrix; also, there need not be an immobilization of any complex. These reaction stations are aligned along a matrix that has pockets within the matrix itself, such that reactants may be added to and confined in these pockets, thereby forming reaction stations. Probe complex and displacement complex formation can occur in these stations. These complexes can be physically separated by being in different reaction stations. The transfer from one station to the next can occur by mechanical transfer using, for example, a pipette. Transfer can also occur through the matrix, for example, by gravitational flow, electrically induced endosmotic flow, wetting, capillary action, pump flow and electrically induced electrophoretic flow. The support matrix itself can be a chromatographic support in the form of beads or particles, thin-layer plates, membranes, polyacrylamide gels, starch gels, agarose gels and other polymeric gels.

The multiple sequential polynucleotide displacement reactions described herein can be used as diagnostic methods for example, to detect the presence of, or absence of, polynucleotide sequences representative of bacteria, viruses, fungi and plant material in a biological. For any polynucleotide of known nucleotide sequence, polynucleotide probes can be designed as described herein. Using the methods described herein, one, or more polynucleotides representative of pathogenic or contaminating biological material can be detected. For example, to detect the presence of the human immunodeficiency virus (HIV) in a blood sample, polynucleotides can be designed as described herein that are complementary to and will hybridize with a polynucleotide sequence representative of HIV, thus detecting the presence of HIV in the biological test sample. The biological test sample can be used directly in the methods described herein or "prepared" for assay using methods well known to those of skill in the art (e.g., lysing cells to obtain the DNA or RNA present in the test sample or filtering or centrifuging the test sample). Another example is where it is desirable to detect a specific mutated region in the genome of an individual (or animal or plant). Some genetic mutations occur due to the insertion of nucleotide sequence into a host's genome. Polynucleotides can be designed as described herein that are complementary to and will hybridize to a nucleotide sequence representative of an insertion sequence, thus detecting the insertion sequence within the host's genome. One of ordinary skill in the art will be familiar with preparing a biological test sample for such an analysis.

In another embodiment, the invention pertains to using Cascade displacement to amplify the target polynucleotide molecule. This method involves a sequential series of probe complex and displacement complex formation. (See, U.S. Ser. No. 09/188,086; the entire teachings of which are incorporated herein by reference).

A first probe complex is formed by contacting a first polynucleotide sequence with a second polynucleotide sequence under conditions suitable that will facilitate chemical hybridization between the first and second polynucleotide sequence. Preferably, the first polynucleotide sequence has a high degree of complementarity, therefore high affinity, with the target polynucleotide sequence as compared to the second polynucleotide sequence range of 95–100%.

A first displacement complex is formed by contacting the first probe complex with a target polynucleotide sequence (which is a nucleotide sequence contained within the target polynucleotide molecule and referred to herein as target third polynucleotide sequence) under conditions suitable to facilitate the displacement by and hybridization of the target third polynucleotide sequence. Preferably, the first polynucleotide sequence of the complex has a higher affinity for the target third polynucleotide sequence than with its second polynucleotide sequence complex partner. Based on this affinity difference, the target polynucleotide sequence will compete off at least one second polynucleotide sequence from the first probe complex. A new complex results having the first and target polynucleotide sequences hybridized together via base-pairing, while the second polynucleotide sequence is displaced.

This probe and displacement complex cycle is followed by a second cycle of probe and displacement complex formation. The second probe complex is formed by contacting a fourth and fifth polynucleotide sequence under conditions suitable for hybridization. Preferably, the fourth polynucleotide sequence has a higher affinity for the displaced second polynucleotide sequence than for its fifth polynucleotide sequence complex partner. The second displacement complex is formed by contacting the second probe complex with the displaced second polynucleotide sequence which is the product of the first displacement reaction. Given that the fourth polynucleotide sequence has greater affinity for the displaced second polynucleotide sequence than for its fifth polynucleotide sequence partner, at least one fifth polynucleotide sequence will be competed off from the second probe complex by the displaced second polynucleotide sequence. As a result of this displacement event, a new complex will be formed between the fourth and second polynucleotide sequence leaving the fifth polynucleotide sequence free. This fifth polynucleotide sequence can now generate a signal which is subject to detection. For example, this fifth polynucleotide sequence can be embedded within a nucleic acid that can be labeled with, for example, a radioactive phosphate atoms that can be detected.

Alternatively, if more cycles are contemplated, then this fifth polynucleotide sequence could serve as a displacing polynucleotide sequence in a subsequent displacement complex. By continuing the cycles, the amplification of the signal(s) is effectuated. Also, If multiple polynucleotide sequences are employed, for example, more than two fifth polynucleotide sequences used in complex formation, this multiplication will continue throughout the assay amplifying the assay signal.

Further cycles of probe complex and displacement complex formation are also envisaged in this embodiment which serve to amplify the signal(s) generated. Probe complexes are formed by successive polynucleotide sequences under conditions suitable for hybridization as articulated for the formation of the probe complexes above. Preferably, at least one member of the complex will have greater affinity for the displaced nucleotide, that was generated during a previous cycle of displacement, than for its current hybridization partner. The member of the complex that has a high affinity for the displaced polynucleotide sequence is referred to herein as the cognate polynucleotide sequence. A cognate polynucleotide sequence is that sequence which preferably is from about 95% to about 100% complementary to a second polynucleotide sequence and will hybridize to the second polynucleotide sequence under from about medium to about high stringency conditions which are well known to the art. This probe complex formation is then followed by a round of displacement complex formation. In this round, the probe complex just created is contacted by a displaced polynucleotide sequence that was generated in a previous cycle, preferably in the immediately preceding cycle. Preferably, at least one member of the complex has a higher affinity for the displaced polynucleotide sequence that for any constituent polynucleotide sequence in the complex. Based on affinity differences, the displaced polynucleotide sequence will displace a at least one polynucleotide sequence hybridized in the probe complex and hybridize to its cognate polynucleotide sequence forming a new complex. The new displaced polynucleotide sequence can then generate a signal which can be detected for the current assay (e.g, a detectably-labeled polynucleotide).

This embodiment also pertains to the use of multiple repeating units of polynucleotide sequences for amplifying the assay signal. In this aspect of the embodiment, the second and fourth polynucleotide sequences contain multiple repeating units of identical sequence per unit, wherein these repeating units are complementary as between the second and fourth polynucleotide sequence. The relationship between the second and fourth polynucleotide sequences is such that they could base pair with respect to their respective repeating units. The fifth polynucleotide sequence, or at least a portion of it is substantially identical (from about 95% to about 100%), to at least one repeat unit of the second polynucleotide sequence. As the assay reaction cycles progress from the first probe complex, multiple fifth polynucleotide sequences will be generated per target polynucleotide sequence assayed and hence multiple signals will be generated.

In another embodiment of the Cascade reaction, a method for detecting a target polynucleotide sequence in a nucleic acid molecule within a sample using a recursive cycle comprising multiple sequential polynucleotide displacement is disclosed. In this particular embodiment, cycles of probe complex and displacement complex formation occur in which complex reactants are generated that allow for the recycling of the assay, thereby generating multiple signals.

A first probe forming complex is generated by contacting a first polynucleotide sequence with a second polynucleotide sequence under conditions suitable for hybridization. Preferably, the first polynucleotide sequence has a higher degree of affinity for the target third polynucleotide sequence as compared to its second polynucleotide sequence complex partner. A first displacement complex is formed by contacting the first probe complex with a target third polynucleotide sequence. This target polynucleotide sequence will displace the second polynucleotide sequence and hybridize to the first polynucleotide sequence due to the affinity between the target and first polynucleotide sequences. The second polynucleotide sequence will be displaced and remain free of the complex now formed between the first and target polynucleotide sequences.

This probe and displacement complex cycle is followed by a second cycle of probe and displacement complex formation. The second probe complex is formed by contacting a fourth and fifth polynucleotide sequence under conditions suitable for hybridization. Preferably, the fourth polynucleotide sequence has a higher affinity for the displaced second polynucleotide sequence than for its fifth polynucleotide sequence complex partner. Preferably, the fifth polynucleotide sequence is partially identical (from about 95% to about 100%) to the target polynucleotide sequence. The second displacement complex is formed by contacting the second probe complex with the displaced second polynucleotide sequence which is a product of the first displacement complex. Given that the fourth polynucleotide sequence has greater affinity for the displaced second polynucleotide sequence than for its fifth polynucleotide sequence partner, at least one fifth polynucleotide sequence will be competed off from the second probe complex by the displaced second polynucleotide sequence. As a result of this displacement event, a new complex will be formed as between the fourth and second polynucleotide sequence leaving the fifth polynucleotide sequence free. This fifth polynucleotide sequence can now generate a signal which is now subject to detection. For example, this fifth polynucleotide sequence can be embedded within a nucleic acid that can be labeled with, for example, a radioactive phosphate atoms that can be detected. Alternatively, this fifth polynucleotide sequence can serve as a displacing polynucleotide sequence in the next displacement complex.

A third probe complex is formed by contacting a sixth polynucleotide sequence with a seventh polynucleotide sequence under conditions suitable in an aqueous medium for hybridization between the sixth and seventh polynucleotide sequences. Preferably, the degree of homology between the seventh polynucleotide sequence and the target polynucleotide sequence is from about 95% to about 100%. Most preferably, the seventh polynucleotide sequence is the target third polynucleotide sequence. The sixth polynucleotide sequence preferably has a higher affinity for the displaced fifth polynucleotide sequence than for its hybridization partner.

A third displacement complex is formed by contacting the third probe complex with the displaced fifth polynucleotide sequence under conditions suitable for the displacement of at least one seventh polynucleotide sequence from the probe complex and the hybridization to the sixth polynucleotide sequence by the fifth polynucleotide sequence. The displaced seventh polynucleotide sequence can now be cycled back to the first displacement complex, thereby initiating the entire sequence of cycles again. This generation of seventh polynucleotide sequences, as well as any other multiple displaced polynucleotide sequences, can serve to generate signals.

A recursive cascade of displacement reactions with gain of signal at each individual displacement reaction can be used to achieve high levels of amplification. The probe complexes are designed to provide a two-fold gain of signal for each displacement reaction. The total amplification achieved by a single cycle of three displacements with twofold gain of signal at each step is eight-fold. Each additional cycle of three displacements will further increase signal by eight-fold.

The invention also pertains to a reverse displacement method and uses a reagent complex composed of two nucleic acids: a "probe" nucleic acid and a "tether" nucleic acid. In this complex, the probe is complementary to the target nucleic acids. The tether nucleic acid is complementary to a specific subsequence of the probe nucleic acid. The tether nucleic acid is therefore identical, or substantially similar in sequence, to a specific subsequence of the target. In a preferred embodiment of the invention, the probe nucleic acid is detectably labeled.

When this complex is combined in solution with the target nucleic acid under suitable conditions, the single-stranded region of the probe nucleic acid will hybridize with the target, and the probe nucleic acid be displaced from the tether nucleic acid by homologous strand exchange. The product of the reverse displacement reaction is a hybrid between the probe nucleic acid and the target.

The product of the reverse displacement reaction is clearly different from the product of the standard displacement reaction described by Diamond et al., in which the detectable product is the single-stranded signal nucleic acid. (See, U.S. Pat. No. 4,766,062).

When the tether nucleic acid is immobilized on a solid support, or is supplied in a potentially immobilizable form, the reverse displacement assay retains the operational simplicity of standard diplacement assays. If the tether is immobilized, the hybridization of the probe nucleic acid to target will cause a release of the probe-target hybrid into solution, and subsequent separation of the phases will allow easy assay of the complex in the solution phase. If the tether contains an affinity tag, separation of displaced probe from non-displaced probe can be achieved following capture of the affinity tags on solid support material containing binding ligands specific for the tag.

A key advantage of reverse displacement over standard displacement, is that in reverse displacement there is no need to saturate the tether nucleic acid with labeled probe nucleic acid. Uncomplexed tether will not hybridize with the target and therefore cannot compete with target for hybridization with probe nucleic acids. In fact, since uncomplexed tether nucleic acids can hybridize to probe nucleic acids that have been released in a target-independent manner, they can actually help to reduce background. Furthermore, unhybridized tether nucleic acids cannot hybridize with authentic probe-target hybrids, unlike the corresponding situation in the standard displacement reaction. (See, U.S. Ser. No. 60/103,075 Now U.S. Pat. No. 09/411,777 ; the entire teachings of which are incorporated herein by reference).

The amplified sequence is labeled either during amplification or following the procedure, thereby at least one target molecule is labeled. There are a variety of different probe-labeling systems that can be employed in the present invention. The label can include, but is not limited to, radioactivity, fluorophores, luminescence probes, chromophores, affinity reagent or enzyme.

In one embodiment, dual fluorescent probes that hybridize to adjacent regions of the target molecule, thereby permitting detection by fluorescence resonance energy transfer (hereinafter "FRET") can be used. The probes can be designed to hybridize to adjacent regions of a target polynucleotide. The fluorophores attached are designed to participate in FRET in such a manner that one acts as a "donor" which can be excited at a wavelength range which is well below the excitation spectrum of the second "acceptor" fluorophore. When both probes are hybridized to a target polynucleotide, the excited state donor fluorophore can donate excitation energy in a non-radiative energy transfer event with the acceptor probe which is held in close proximity to the donor by its hybridized nucleic acid probe. The excited acceptor fluorophore can then decay by fluorescence at a wavelength range that is at least partially distinct from the emission spectrum of the donor fluorophore. By monitoring emission over this distinct region of the acceptor fluorophore, the FRET emission of the fully hybridized target complex (comprising the target polynucleotide and nucleic acid probe with attached fluorophores) can be distinguished from the emission of non-hybridized (or singly-hybridized) probes. Since FRET is dependent on the inverse sixth power of the distance between the probes, unhybridized probes should produce a diminutive background signal. Furthermore, target specificity is high since a positive signal depends on the simultaneous hybridization of two different probes. (See, Mergny, J., et al., *Nucleic Acid Res.,* 22:920–928 (1994); the entire teachings of which are incorporated herein by reference).

In a preferred embodiment, the probes are present at relatively high concentrations to ensure that all target molecules are rapidly and completely hybridized with probes containing the fluorophores. Preferably, each probe is present at a concentration from about 0.001 μM to about 100 μM. More preferably, the probes are present at concentrations from about 0.01 μM to about 10 μM.

In another embodiment, the FRET probes can be used in the presence of lysing reagents. By employing guanidine thiocyanate (GuSCN), guanidine HCl (GuHCl) and other common chaotropes used for cell lysis, it is possible to use the FRET probes directly. Additionally, hybridization can be accomplished in the cell lysis compartment for direct detection of the target molecule in a single compartment. (See, Thompson and Gillespie, *Anal. Biochemistry*, 163:281–291 (1987); Van Ness, J. et al., *Nucleic Acid Research*, 19:3345–3350 (1991); Van Ness and Chen, *Nucleic Acid Research*, 19:5143–5151 (1991); the entire teachings of which are incorporated herein by reference).

In another embodiment, Beacon probes can be used to detect at least one target polynucleotide. Beacon probes are commercially available (Perkin Elmer, Calf.). Beacon probes are small, usually synthetic oligonucleotides that contain a fluorophore ("F") and a quencher ("Q"). The fluorphore and quencher are present at spatially distinct locations within the nucleic acid probe. In the absence of a target polynucleotide, the probes are designed to have some intramolecular secondary structure that preferably brings the fluorophore into close proximity with the quencher. This proximity holds the fluorophore in a "dark" nonfluorescent state since the quencher ensures that all excited fluorophores decay non-fluorescently. However, if the probe becomes hybridized to its complementary polynucleotide target, then the intramolecular structure of the unhybridized beacon (F and Q) becomes replaced with the intermolecular secondary structure of the target-probe hybrid. In this hybrid, the fluorophore and quencher are kept separated by the stiff duplex formed between the target polynucleotide and probe such that the quencher is no longer able to quench the fluorophore. (See, Tyagi, S. and Kramer, R., *Nature Biotechnology*, 14:303–308 (1996); the entire teachings of which are incorporated herein by reference).

In another embodiment, the target molecule is a polypeptide or protein. As used herein, the term polypeptide is meant to denote a shorter version with respect to the number and content of amino acid residues of a given mature protein, or a biological polymer comprising amino acid residues linked via polypeptide bonds having about 3 to about 150 amino acid residues in length. These biomolecules can serve as target molecules of the current invention. Polypeptides and proteins can be produced by from cellular organisms, such as exotoxins released by certain bacteria. These biomolecules can also be liberated from a cellular organism by treating the organism with at least one lysis reagent. Once the cell membrane (or cell wall) is lysed, these biomolecules can be liberated from the constraint of the cell membrane (or cell wall).

In one embodiment, antibodies, or antibody fragments, such as the Fab portion of the antibody, produced against a specific target molecule, for example, a specific polypeptide or protein, can be used to detect that target molecule. Methods are well known to those skilled in the art, such as radioimmunoassay (RIA) or enzyme-linked immunoabsorbant assay (ELISA) for detecting target polypeptides or proteins. (See, See, Ausubel, F. M., et al. (eds.), *Current Protocols in Molecular Biology*, Greene Publishing Associates and Wiley-Interscience, 5$^{th}$ ed., (1991), vol. 2, pp. for RIA: 11.1.4., 11.16.10–11.16.11; for ELISA: 11.2.8; the entire teachings of which are incorporated herein by reference).

The primary, or capturing, antibody can be associated with the surface of a compartment. The antibody can be covalently attached, for example, using a carbodiimide preparation. The biological sample can be passed through the compartment containing the primary antibody and the target polypeptide, protein, or fragment thereof can interact with its cognate primary antibody. After allowing for the interaction between the primary antibody with its antigen, a secondary detectably-labeled antibody can be introduced that will interact with the primary antibody, resulting in a sandwich-like structure.

In one embodiment, the invention pertains to a device for detecting the presence, or absence, of a target molecule in a biological sample comprising a receptacle housing at least one reaction chamber comprising at least one compartment, wherein the compartment(s) comprises at least one bacterial vital staining reagent. In this embodiment, the invention pertains to a device and method for detecting the presence, or absence, of a target molecule in a biological sample for the presence of bacteria. The bacterial cells of the biological sample are subjected to staining using vital bacterial stains that can detect a specific genius and/or species of bacteria. No lysing is required in this embodiment. The bacteria can be stained based upon their components. Vital stains include, but are not limited to, Gram stain, acid-fast stain, flagella stain, spore stain and metachromatic granule stain. The reaction chamber can comprise compartments comprising at least one reagent used to stain at least one bacteria, if present. In one embodiment, the device can be attached to a sample collection unit housing a biological sample. In another embodiment, the device is unattached from any sample collection unit and comprises an entry orifice in which a biological sample can be introduced through a portal into the reaction chamber of said device.

In one embodiment, the target molecule is in sufficient amount so as to be amenable to detection using the methods described herein absent amplification. A sufficient amount refers to the target molecules concentration in the biological sample being analyzed, wherein the concentration of the target molecule is high enough for detection without the employment of amplifying the target molecule. Initially, if the amount of the target molecule in an aliquot obtained from a biological sample is insufficient, then suitable methods for concentrating the sample can be employed. These suitable methods for concentrating samples are well known to the art and can include, but not limited to, lyophilization, concentrating a sample using membrane filters of certain molecular weight screening, etc. Therefore, there is no concomitant need for reagents used to inactivate amplification inhibitors.

In another embodiment, the target molecule is the intact cellular species, for example, a bacteria, virus or parasite, in which no lysis is required. This can also be true for elaborated molecules such as exotoxins from certain strains of bacteria or other released factors, including polypeptides and proteins from other organisms. If present in sufficient amount, then these target molecules can be detected employing the methods described herein.

This invention pertains to methods of detecting the presence, or absence, of a target molecule. In one embodiment, the invention pertains to a method for screening a biological sample for the presence, or absence, of at least one target molecule in a biological sample, wherein the target molecule is a nucleic acid. In another embodiment, the target molecule is a polypeptide or protein. The methods can include detecting the presence of a target molecule. In one embodiment, the target polynucleotide is detected using a nucleic acid probe. In one embodiment, the nucleic acid probe is a beacon probe. In one embodiment, the target polypeptide or protein is detected using an antibody, or antibody fragment, specific for the target polypeptide or protein, or fragment thereof.

The current invention provides for fast and reliable devices and methods for detecting the presence, or absence, of a target molecule in a biological sample. These devices and methods can be employed in a variety of milieus including situations where a technically sophisticated laboratory is not present and not easily accessible.

The features and other details of the invention will now be more particularly described and pointed out in the examples. It will be understood that the particular embodiments of the invention are shown by way of illustration and not as limitations of the invention. The principle features of this invention can be employed in various embodiments without departing from the scope of the invention.

EXAMPLES

Example 1
A Piston-Mediated Device with PCR

Figure 5:
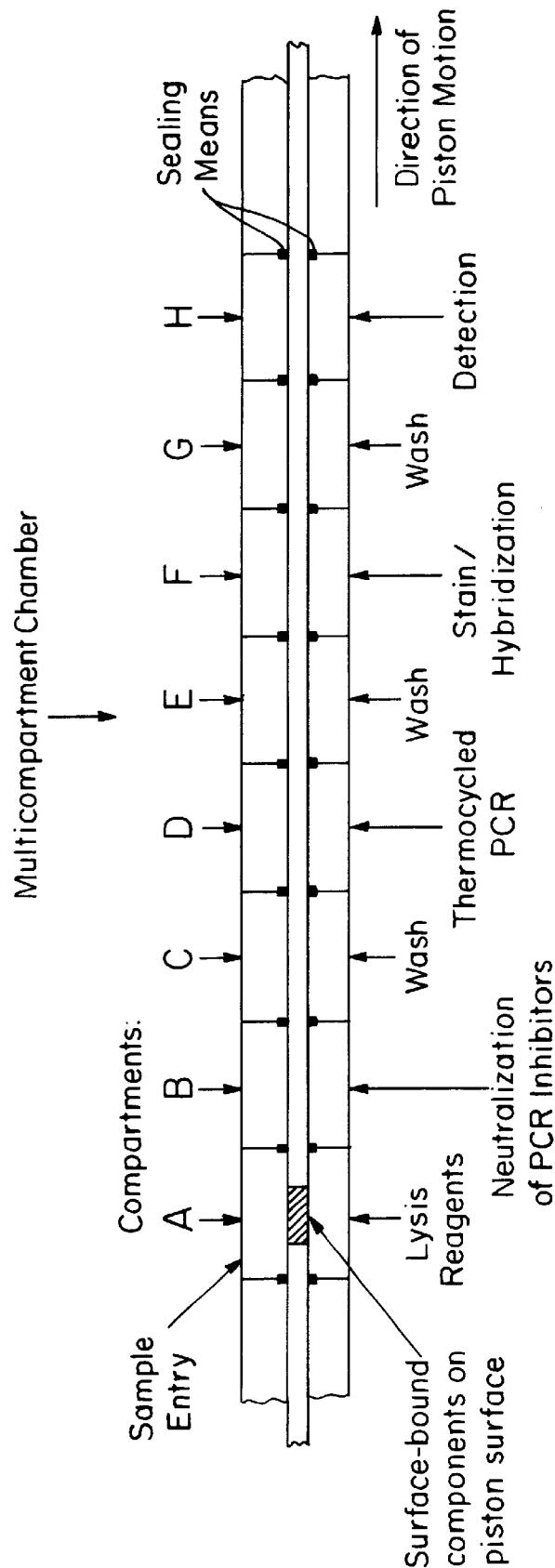
FIG. 5 depicts a schematic representation of some of the components of the device of the present invention used for nucleic acid analysis.

In one embodiment of the invention a piston comprising surface bound reagents is moved within a chamber comprising multiple compartments. (See FIG. 5). One or more of the compartments contain reagents either in liquid form or in dry form such that they can be dissolved into solution by the addition of liquid, such as a buffer. A nucleic acid analysis utilizing the Polymerase Chain Reaction (PCR) is performed with surface-bound primers with said primers bound to the end of the piston as depicted.

To begin the analysis, optionally liquid may be added to one or more of the compartments to dissolve reagents not initially in solution. Compartment A optionally can initially contain blood cell lysis reagents, together with other reagents to promote the analytical reactions to follow, either previously placed there or so located during the analysis. A sample of blood, or other body fluid containing nucleic acid material, is added to compartment A. The lysis reagents cause cells within the sample to rupture and release their contents into the solution within the compartment. A period of time form about 10 to about 60 minutes is then allowed for the nucleic acid in solution to anneal to the surface-bound primers if there exist nucleic acid species in the applied sample with sequence complementarity to the primers.

When sufficient time (approximately 10 to 60 minutes) has elapsed for primer annealing to have occurred, the piston is withdrawn such that the end with surface-bound primers and potentially annealed nucleic acid species is moved into compartment B. The piston moves through a sealing means such as a plastic or rubber seal loosely fitting the piston which permits the piston to pass through with minimal or acceptably low liquid leakage between compartments but without disturbing the surface sufficiently to unacceptably degrade the analysis in progress. Compartment B contains reagents which counter or neutralize the inhibitory effects of the components in compartment B which would inhibit nucleic acid amplification by PCR. The piston is positioned with its surface-coated region within compartment B for sufficient time (approximately 10 seconds to 10 minutes) to neutralize the PCR inhibitory effects of components in solution.

When the neutralization of PCR inhibitors is thus sufficiently complete, the piston is then withdrawn further such that the surface-coated region passes through another similar sealing means into compartment C. This contains a solution which serves to replace the solution in compartment B and to wash the surface-bound region of the piston to remove unbound components from the surface. The piston remains so positioned until the washing process has progressed adequately to support the remaining analytical steps.

When the washing process in sufficiently complete, the piston is then withdrawn further so that the surface-coated region passes through another sealing means into compartment D. This contains a solution of reagents that support the PCR amplification method. When the region of the piston comprising surface-bound primers with annealed nucleic acid species is positioned with compartment D, conditions are applied to cause PCR amplification to occur. Such conditions are well known and include the presence of appropriate reagents and temperature cycling for appropriate periods between typically three temperatures to cause primer extension, denaturation and annealing to occur. When sufficient amplification has occurred to cause a useful or desired quantity of amplified nucleic acid to have been formed, the temperature cycling can be stopped.

When the amplification process is sufficiently advanced, the piston is then withdrawn further such that the surface-coated region passes through another sealing means into compartment E. The reagents in this compartment provide a further washing process by replacing the components in compartment D and removing non surface-bound components from the piston surface. The piston remains so positioned until the washing process has progressed adequately to support the remaining analytical steps.

When the present washing process in sufficiently complete, the piston is then withdrawn further so that the surface-coated region passes through another sealing means into compartment F. This contains a solution of reagents that prepare the piston surface for detection of amplified DNA that is attached to the surface where surface-bound primers were previously located. Said reagents can include nucleic acid stains of which a wide range are now known and a broad selection is commercially available, such as ethidium bromide or Syber Green (Molecular Probes, Eugene, Oreg.). Alternatively, such reagents can include hybridization probes with sequence homology matched to amplified nucleic acids expected to be now present as surface-bound amplificate, where such probes can usefully be conjugated with a label being a chemical moiety that is detectable by known means. For situations where more than amplified nucleic acid species may be represented as a surface-bound amplificate, more than one such hybridization probe can be so provided, advantageously with differing detectable labels. The piston remains at this position until sufficient time has elapsed for the staining or hybridization process to be completed to a useful or desired extent.

The piston is then further withdrawn such that the region with stained and/or hybridized surface-bound amplificate passes through another seal into compartment G. This contains a solution of reagents such as buffers that serve as a further washing process by removing non surface-bound reagents from the piston surface.

When this washing process is adequately complete, the piston is further withdrawn through another seal into compartment H. This serves as a detection chamber, where surface-bound amplificate on the piston surface may be detected by a variety of known means by optical access through a region of the boundary of compartment H having acceptable optical transparency. Such optical detection may be by colorimetric analysis of the piston surface and stains and/or detectable labels there located, such as by any known spectroscopic technique. Detection may be by fluorescence of a nucleic acid stain or of a label conjugated to a hybridized probe. Alternatively, such label can be an enzyme causing an optically detectable signal, such alkaline phosphatase acting on umbelliferyl phosphate and converting this to fluorescent umbelliferone, or by acting on other substrates such as give rise to, for example, a chemiluminescent signal. A variety of techniques for detecting nucleic acids are known to those skilled in the art.

If an appropriate optical signal is detected, this implies that amplificate is now present on the piston surface following successful PCR amplification. This implies that the applied sample contained nucleic acid species having homology with the surface-bound primers. Thus, with appropriate primer selection, a particular target nucleic acid sequence may be defined by the pair of primers used for its amplification. Therefore, the presence of amplificate derived from these primers indicates the presence of the target nucleic acid sequence in the applied sample.

The example may be extended to cover the simultaneous amplification and detection of several nucleic acid species in parallel. Two or more sets of primer pairs can be surface-bound on the piston surface, each such pair being prepared to amplify a particular target nucleic acid sequence. The sets of primer pairs can intermix such that two or more nucleic acid species are amplified as a surface-bound mixture. Alternatively, each primer pair can be attached to a distinctly separated area of the piston surface. In addition, separate areas of the piston surface can each have pairs of surface-mounted primers intermingled thereon. If the surface-bound primer pairs are spatially separated, the resulting surface-bound amplificates will be similarly separated and thus can be optically distinguished by their differing position, such that multiple amplificates may be detected simultaneously. If the sets of surface-bound primer pairs are intermingled, such that the resulting amplificates are similarly intermixed, these, then, may be optically distinguished such as by each being hybridized to specific labeled probes where the labels are optically distinguishable. Such distinguished optical detection can be accomplished by scanning the appropriate region of the piston surface, or by imaging all or part of the surface onto a charge coupled optical detection device, or other linear or area sensitive detector.

Various means can be applied to assist with the series of chemical reactions collectively comprising the analysis. Thus the entire chamber can be moved, vibrated or agitated in some manner as to assist with the mixing of reagents, and/or the replacement of liquid which would otherwise be motionless and could become exhausted at the reaction surface. As one mode of such agitation, the position of the piston can be cycled over some range within any chamber, to assist with liquid mixing and refreshment of reagents at the reaction surface.

This example provides for a number of compartments, including several providing for washing stages. For some analyses, not all such stages and compartments are necessary. Thus, for example, in some cases the wash step between amplification and staining or hybridization can be unnecessary, as may also be the wash between amplificate staining and detection can be unnecessary.

The piston and the compartments can have approximately circular cross sections. However, other form factors can be used. It is particularly advantageous for the piston to have, for example a flat surface area to which the primers are bound, such that at the detection stage this surface can be readily inspected optically and, in particular, with two or more separate amplification areas that these can be straightforwardly optically imaged onto a planar detector.

This example describes in detail the amplification of nucleic acid species PCR. This can also be achieved by a variety of alternate amplification schemes such as by the Ligase Chain Reaction (LCR) and by other known amplification schemes.

Figure 6:
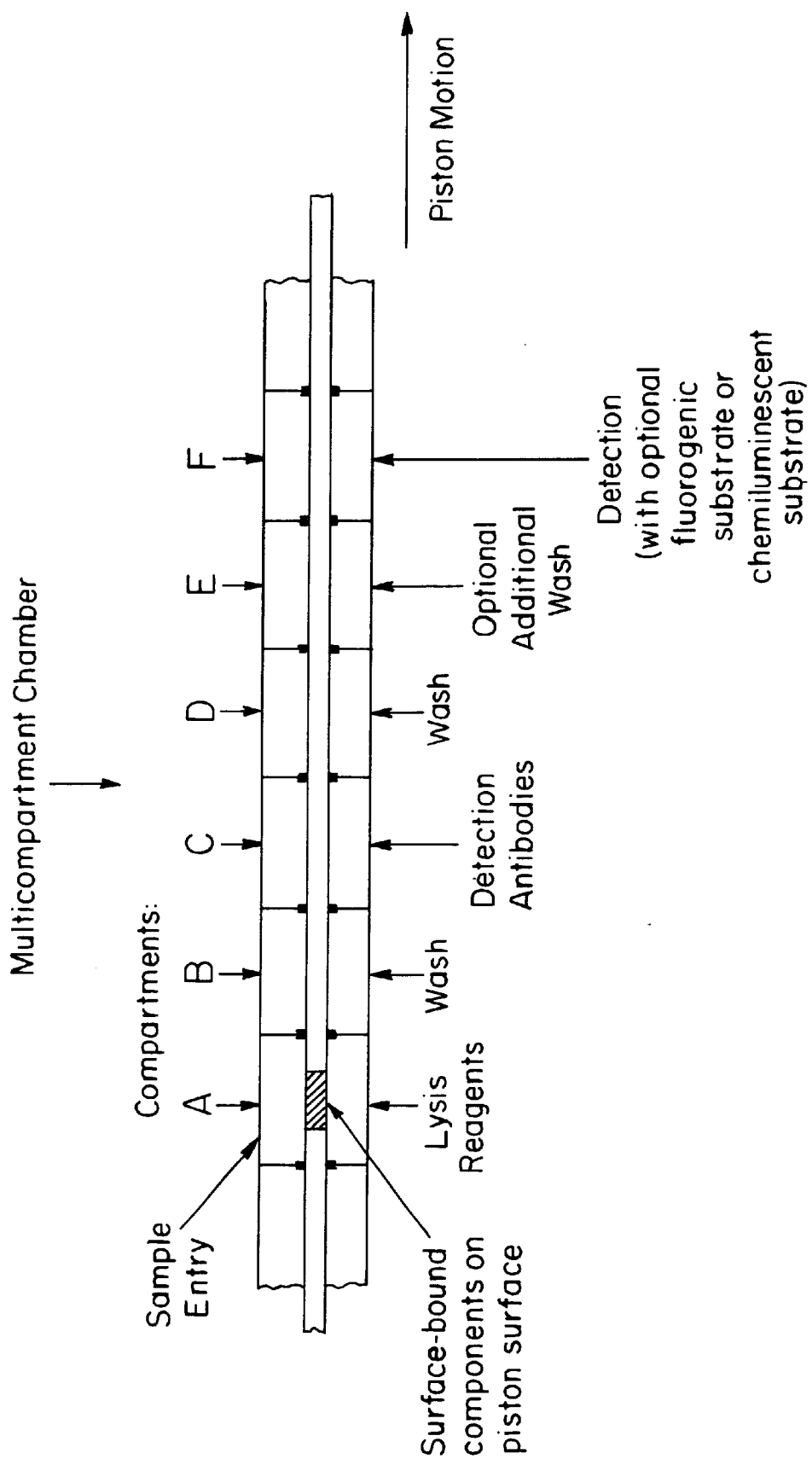
FIG. 6 depicts a schematic representation of some of the components of the device of the present invention used for immunoassay analysis.

An alternative embodiment is depicted in FIG. 6. This figure illustrates the refinement that the surface-binding site or sites are positioned away from the end of the piston. The free end of the piston is long enough to extend from the compartment wherein the current analytical reaction is occurring back to at least the previous compartment. As the piston remains positioned in the seal leading from the previous compartment, this reduces liquid leakage. Thus, the active surface of the piston with surface-mounted primers, is essentially isolated from the two adjacent chambers, which greatly reduces the chemical cross-contamination between chambers and renders the washing steps more effective.

The chamber can be made from a variety of materials such as glass silica, polypropylene, plastic, stainless steel or ceramic material. It is particularly beneficial for the chamber to be fabricated from material that is suitable/compatible for a PCR reaction or other nucleic acid amplification technique. Alternatively, one or more compartments of the chamber can have its entire surface coated with material which does not interfere with nucleic aced amplification. Such materials include polypropylene, polystyrene, polymethylmethacrylate and polycarbonate.

Example 2

A Piston-Medicated Device for Immunoassay

Another embodiment of the invention utilizing a piston comprising surface-bound reagents which is moved within a chamber comprising multiple compartments is depicted in FIG. 6. One or more of the compartments contain reagents either in liquid form or in dry form such that they can be dissolved into solution by the addition of a liquid, for eaxample, a buffer. An immunoassay sandwich analysis is performed with one of the antibody pair (that is, the Primary antibody)being surface-bound to an area of the piston to serve as the capture antibody and with a second labeled secondary antibody added during the analysis, according to known analytical methods.

The use of multiple compartments in the chamber to provide consecutive stages of the reaction is similar to Example 1 above. The surface of the piston can be coated in a variety of ways, but the following description covers the case where the coating extends from the end such that the uncoated end and inter-compartment seals minimize or prevent fluid flow into the current compartment from compartments on either side.

To begin the analysis, optionally liquid can be added to one or more compartments to dissolve reagents not initially in solution. Compartment A can optionally contain blood cell lysis reagents, optionally together with other reagents that can promote the analytical reactions to follow, either previously placed or so located during the analysis. A biological sample, such as of blood or other body fluid containing antigens, of interest is added to compartment A. The lysis reagents will cause cells within the sample to rupture and release their contents into the solution within the compartment. A period of time (approximately 2 to 120 minutes) is then allowed for one or more antigens comprising a polypeptide or protein in solution to bind to one or more surface-bound specific antibodies attached to the piston surface.

When sufficient time has elapsed for sample antigens to have bound sufficiently to antigen specific surface-bound antibodies, the piston is withdrawn such that the area with surface-bound antibodies and attached sample antigens is moved into adjacent compartment B. Compartment contains reagents which serve as a wash step to remove solution components not required for remaining steps in the assay and which might inhibit the subsequent steps.

When the washing process is sufficiently complete, the piston is then withdrawn further so that the surface-coated region passes through compartment C. This contains a solution of reagents including labeled secondary antibodies that will bind to the surface-bound antigens of interest. The piston remains in compartment C until the formation of an antibody sandwich around the antigens of interest is sufficiently complete.

When the sandwich formation process is sufficiently complete, the piston is then withdrawn further such that the surface-coated region passes into compartment D. Reagents in this compartment provide a washing process and particularly separate the surface-bound antibody sandwich from free labeled detector antibody remaining in solution compartment C.

The piston with surface-bound antibody sandwich optionally can then be moved through compartment E, wherein a further washing stage can be accomplished. Further washing stages can optionally be inserted at this point.

When the overall washing process in sufficiently complete, the piston is then withdrawn into compartment F which serves as detection chamber. One or more antigens sandwiched between two antibodies on the piston surface can be detected by a variety of known means by optical access through a region of the boundary of compartment F having acceptable optical transparency. Such optical detection can be by calorimetric analysis of the piston surface and stains and/or detectable labels there located, such as by any known spectroscopic technique. Detection can be by fluorescence of fluorescent labels conjugated to labeled detector antibodies. Alternatively, the label can be an enzyme causing an optically detectable signal, such alkaline phosphatase or horseradish peroxidase acting on umbelliferyl phosphate or other fluorescent substrate and converting this to fluorescent umbelliferone or other fluorophore, or by acting on other substrates such as give rise to, for example, a chemiluminescent signal. A variety of techniques for detecting labeled antibodies are known to those skilled in the art.

If an appropriate optical signal is detected, this implies that one or more antibody sandwiches is present on the piston surface following a successful sandwich assay. This implies that the test sample contained one or more antigens for which pairs of antibodies were provided. Thus, with appropriate antibody pair selection, one or more particular target antigens can be detected by formation of sandwiches with antibody pairs for which they serve as antigens. Therefore, the presence of detectable antibody sandwich indicates the presence of the target antigens as components of the applied sample.

The analysis can be extended to cover the simultaneous detection of several sample component antigens in parallel. Two or more capture antibodies may be surface-bound on the piston surface, each being prepared to bind to a particular target sample antigen. The capture antibodies can be intermixed such that the resultant analyte sandwiches are likewise intermixed, with the detection labels differing such that they can be separately detected. Alternatively, each capture antibody can be attached to a distinctly separated area of the piston surface. In addition, separate areas of the piston surface can each have sets of surface-mounted capture antibodies intermingled thereon. If the surface-bound capture antibodies are spatially separated, the resulting surface-bound sandwiches will be similarly separated and thus can be optically distinguished by their differing position, such that multiple sandwiches can be detected simultaneously. If the sets of surface-bound capture antibodies are intermingled such that the resulting sandwiches are similarly intermixed, these can be optically distinguished such as by each being labeled with optically distinguishable labels. Such distinguished optical detection can be accomplished by scanning the appropriate region of the piston surface, or by imaging all or part of the surface onto a charge coupled optical detection device, or by any other known means.

Various means can be applied to assist with the series of chemical reactions collectively comprising the analysis. Thus, the entire chamber can be moved, vibrated or agitated in some way to assist with the mixing of reagents, and/or the replacement of liquid which would otherwise be motionless and could become exhausted at the reaction surface. As one mode of such agitation, the position of the piston can be cycled over some range within any chamber, to assist with liquid mixing and refreshment of reagents at the reaction surface.

This example provides for a number of compartments, including several providing for washing stages. For some analyses, more or less such stages and compartments may be necessary.

The piston and the compartments may have approximately circular cross sections. However, other form factors can be used. It is particularly advantageous for the piston to have, for example, a flat surface area to which the primary antibodies are bound, such that at the detection stage this surface can be readily inspected optically and, in particular, with two or more separate capture areas that these can be straightforwardly optically imaged on to a planar detector.

The chamber may be fabricated from a variety of materials. It is particularly beneficial for the chamber to be fabricated from material that is beneficial for immunoassay. Alternatively, one or more compartments of the chamber can be surface coated with material which does not interfere with immunoassay. In particular, useful such materials are those which do not surface bind antibodies or other proteins in solution.

Example 3

Device with Multiple Compartments and a Roller

Figure 7:
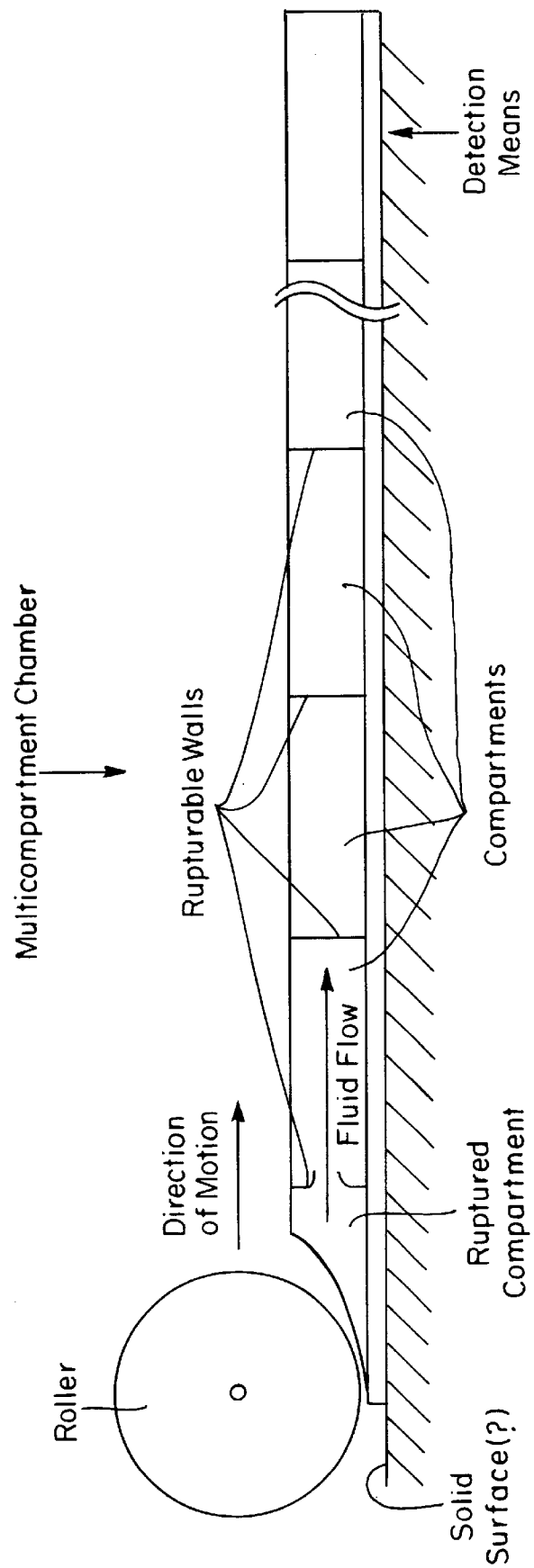
FIG. 7 depicts a schematic representation of employing a roller useful for moving the contents of one compartment into the next.

An embodiment of the invention where an assay of a biological sample is conducted in a chamber comprising multiple compartments is illustrated in FIG. 7. The chamber is constructed of flexible material, for example, a plastic material, such that each compartment may adjust in shape and size. Each compartment is separated from the adjacent compartment by a barrier that can readily be ruptured by application of hydrostatic pressure. A roller is provided to progressively apply pressure to a given compartment in the direction of an adjacent compartment until the barrier ruptures and the contents of the given compartment flow into and are mixed with the contents of the adjacent compartment. Multi-stage assays can be performed thereby.

Figure 8:
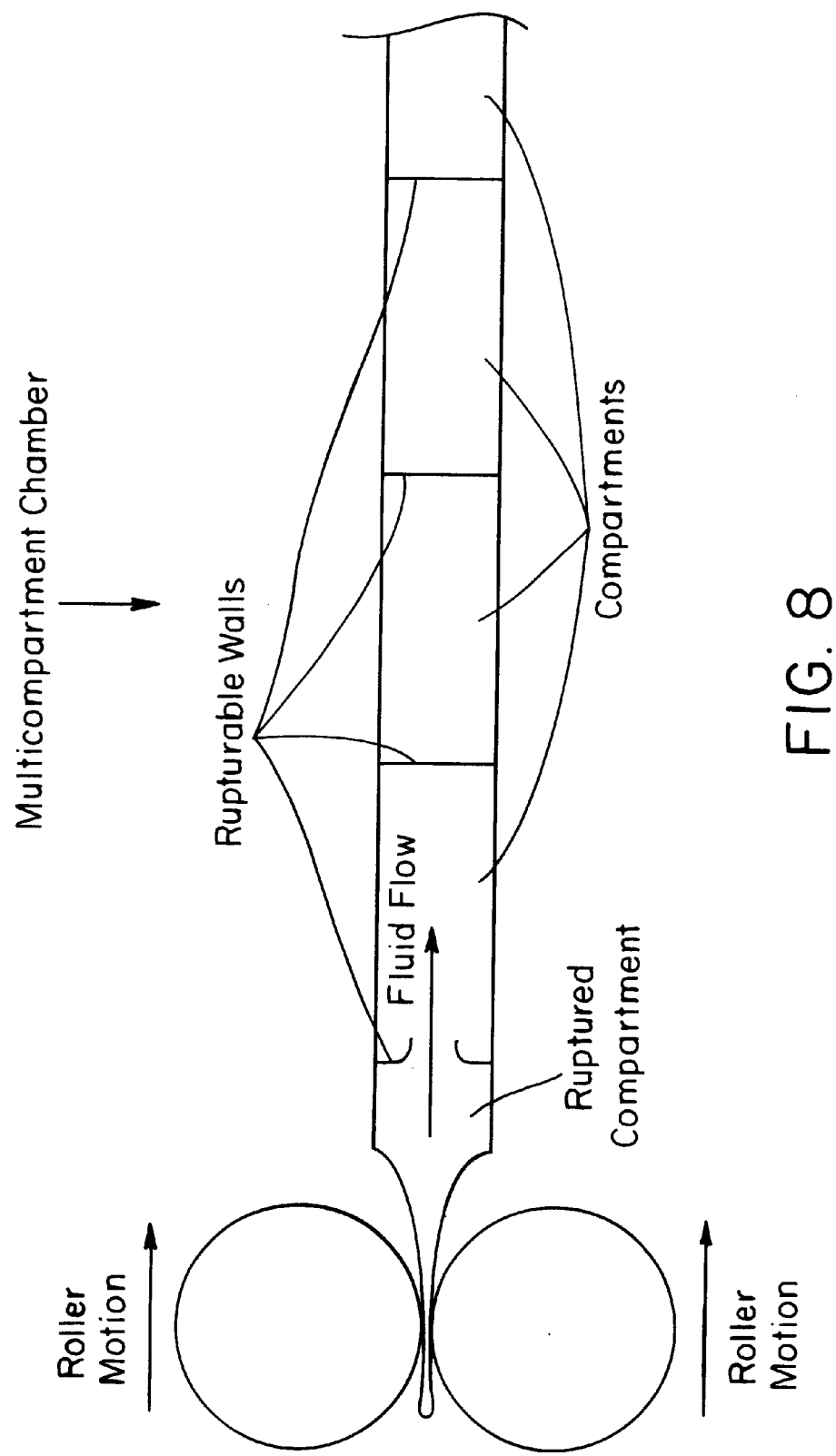
FIG. 8 depicts a schematic representation employing a two roller system facilitating the movement of the contents of one compartment into the adjacent compartment.

FIG. 8 depicts an alternate embodiment where two rollers are employed with contrary rotation, either with both being driven in opposite directions or with one being driven and the other serving as an idler.

Example 4

Device with Multiple Compartments and Plungers

Figure 9:
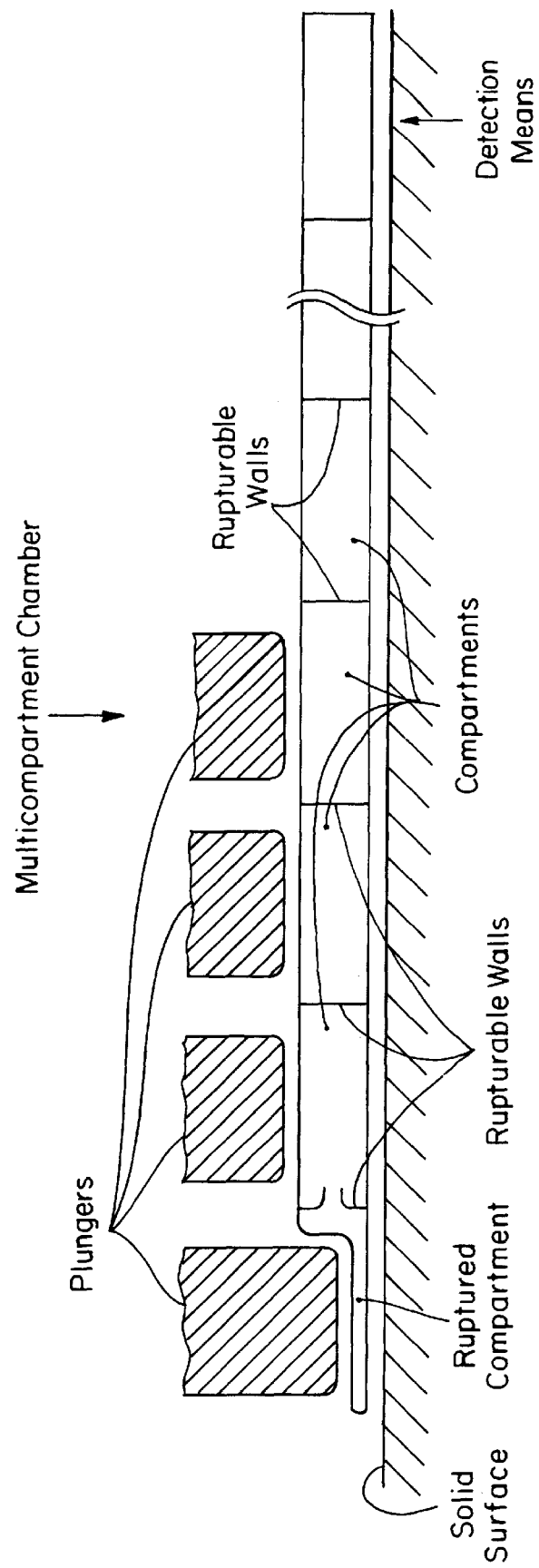
FIG. 9 depicts a schematic representation of employing a plunger system to facilitate movement of contents from one compartment into the adjacent compartment.
Figure 10:
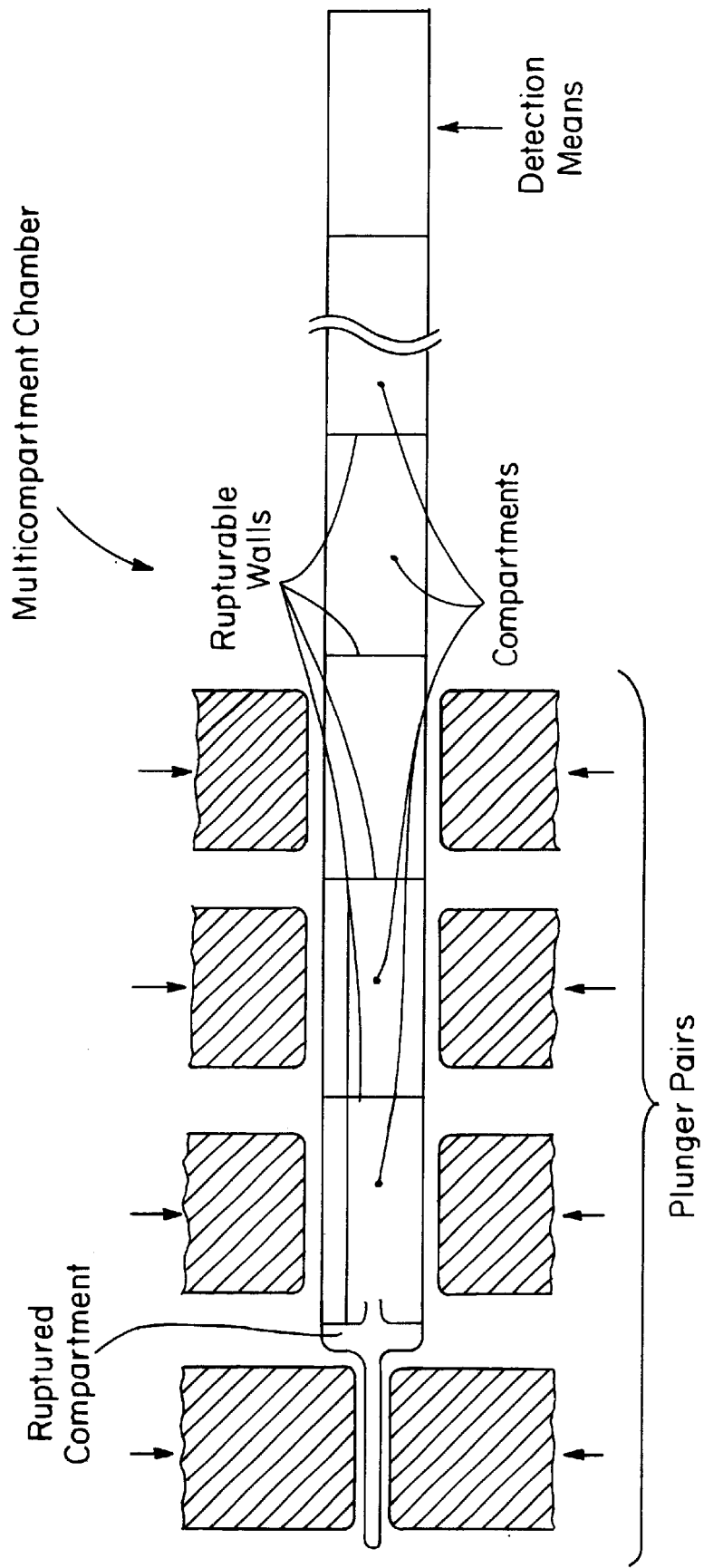
FIG. 10 depicts a schematic representation of employing a plunger system that operates on multiple surfaces of the compartments.

FIGS. 9 and 10 depict alternate embodiments of Example 3. In this case the analytical device again consists of a chamber with multiple compartments being fabricated from flexible material with barriers that can be ruptured between compartments. In this example, fluid is caused to flow between a compartment and an adjacent compartment by the application of a series of plungers that consecutively pressurize individual compartments such that each ruptures and transfers its contents into the adjacent compartment. Each compartment can compressed either between a plunger and a fixed device, or by a pair of plungers moving together to compress the compartment. Alternatively, each compartment can be compressed by a number of plungers, or sets of plungers.

Advantageously, the outer sample collection unit formed around each compartment can be of defined form and volume, to constrain the compartment to maintain this form and volume, optionally until the compartment is compressed or until the sample collection unit is increased in volume such as to permit the compartment therein to expand to accept fluid from an adjacent compartment.

Example 5
Pumped flow Device

Figure 11:
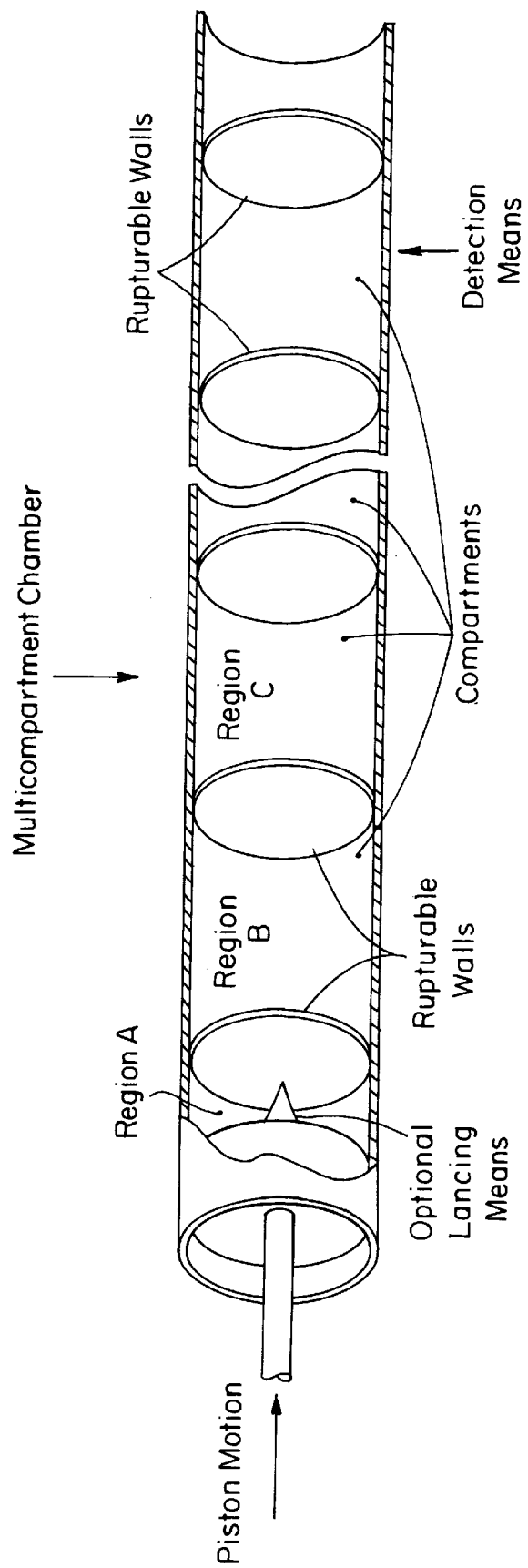
FIG. 11 depicts a schematic representation of a piston pump-mediated movement of material from one compartment into the adjacent compartment.
Figure 12:
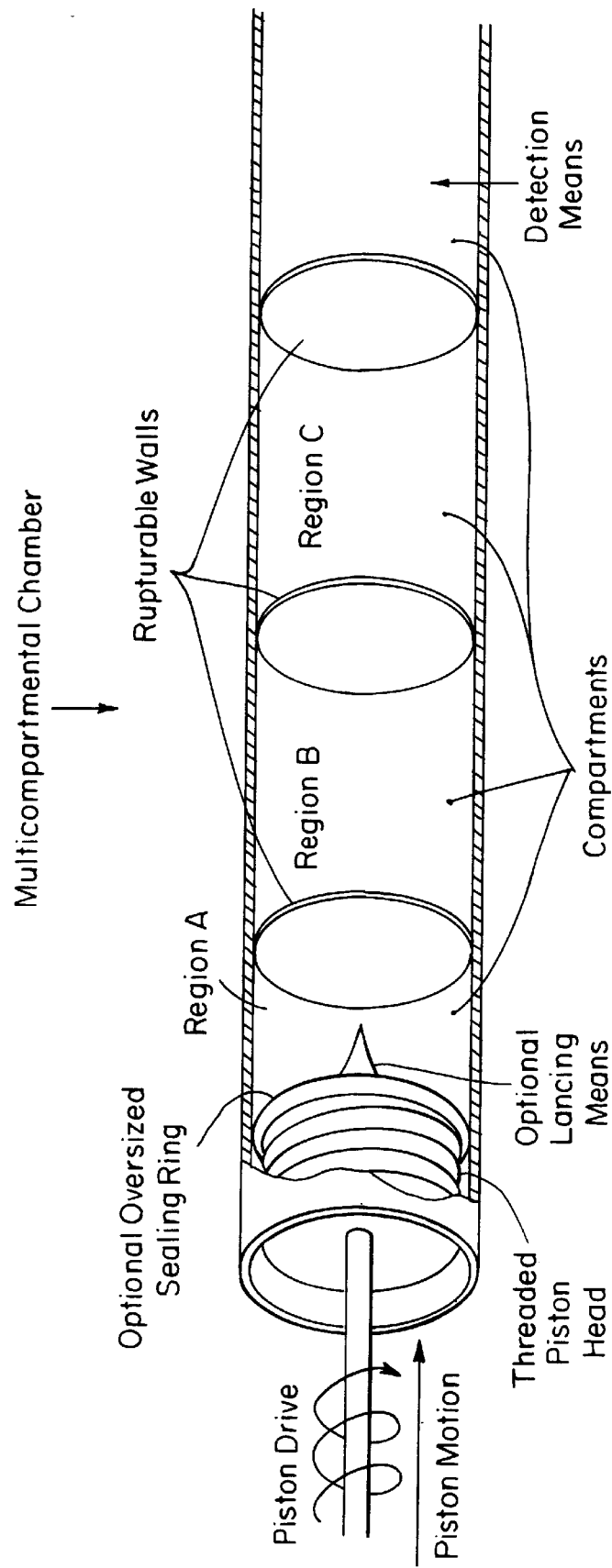
FIG. 12 depicts a schematic representation of a piston pump-mediated device having a threaded piston head.

FIGS. 11 and 12 illustrate an analysis conducted by a device where reagents are transferred between compartments or regions by pumped fluid flow. Such fluid flow can be induced by a liquid pump internal to the device such as a piston pump or by external pumping means (not shown). As one embodiment, the two figures indicate two alternate piston pump schemes.

Initially, the device is prepared for use by preloading one or more of its compartments or regions with reagents or by rehydrating dried or lyophilized components therein. In the depicted embodiment, fluid motion is induced by moving the pump head into the device such that liquid is pushed ahead of the pump head. The pump head can be moved by externally-induced linear motion as depicted in FIG. 12. Alternatively, the head can be moved by externally-induced rotary motion as depicted in FIG. 12 where a screw thread formed in the pump head self-taps its path into the device. Such self-tapping pumping action is particularly advantageous as very low flow rates can be achieved and delivered flow volumes can be readily controlled down to the microliter level.

The device and its pumping means can be designed in the style of a tuberculin syringe, where the pump head can be a tightly fitted plunger, or optionally can be an oversized self-tapping screw-threaded plunger. The device can be in dimensions and form similar to a syringe barrel, and the inter-reaction chamber can be readily implemented by the use of a reaction chamber fabricated with multiple compartments and sealing barriers in between, with reagents (dried or in solution) located in specific regions as appropriate. The reaction chamber is fabricated from relatively weak material, such as thin plastic, which can readily be ruptured with modest levels of hydrostatic pressure, for example, a few atmospheres or by penetration by a solid object. When the reaction chamber has been fabricated and reagents have been inserted in one or more compartments, and the compartments sealed by thermal or ultrasonic welding, use of adhesive materials or the employment of other known techniques. The reaction chamber is then inserted into the barrel and can be readily held in place by a lip formed at an open end of the reaction chamber being held by the end of the device barrel after insertion. When the analytical process is complete, the combination of device barrel and reaction chamber can be disposed of jointly such as to dispose of potential biohazards, or the reaction chamber can be so disposed of while the device barrel may be retained for subsequent use.

A volume, approximately 10–15 $\mu L$, of test sample is inserted in the device conveniently by inserting this into Compartment A as depicted with the pump head initially withdrawn from this compartment, following which the head is reinserted into the device. This results in the sample being sealed within the device, such that any biohazard associated with the sample is thereby contained. The pump head is then advanced until the sample is compressed against the rupturable barrier between Compartment A and Compartment B. This barrier is ruptured by the pressure exerted by the pumped liquid in Compartment A. The rupture of the inter-region barrier can be assisted by a feature on the surface of the pump head, which assists with piercing tearing or cutting the barrier. After the barrier is ruptured, the sample is pumped into Compartment B, at which point pumping is suspended.

With the analysis of a blood sample, Compartment B contains lysis reagents sufficient to lyse blood cells and then release their contents into solution, where such lysis reagents can be dissolved in solution or dried for solution in the incoming liquid sample. Also contained in this region can be other reagents to assist with the analysis processes to follow. A period of tens of seconds to tens of minutes is then allowed to elapse for the mixing and dissolving of the sample and the lysis reagents and for the cell lysing process to be sufficiently complete.

The lysed sample mixture is than transferred to Compartment C by further motion of the pump head and the consequent rupture of the inter-region barrier between Compartment B and Compartment C. Compartment C contains nucleic acid probes which are complementary to one or more sequences of one or more nucleic acid species present in the applied sample. These probes are labeled with detectable labels such as fluorophores or enzymes that can generate fluorescent or chemiluminescent compounds by action on the appropriate substrates per techniques well known to those skilled in the art. It is particularly advantageous to utilize beacon probes, or a pair of FRET probes, in this application, as they permit hybridized probes to be fluorescently detected in solution with minimal or acceptably low interference from non-hybridized such probes. When the contents of Compartment B have been added to Compartment C as above, a period of tens of seconds to tens of minutes is allowed to elapse for the homogenous hybridization process to become sufficiently complete for subsequent detection.

Optical detection of one or more hybridized nucleic acids in the applied sample can be accomplished within Compartment C. Alternatively, the solution containing detectable hybridized nucleic acids can be pumped by means as above into a separate detection region. This can be internal to the analytical device or can be external. Internal detection is accomplished by, for example, irradiating the Detection Compartment with an optical excitation wavelength, for applications where optical detection is utilized.

The embodiment described above can be modified in various ways within the invention.

The cross-section of the piston and barrel may not be circular. Other cross sections can be used for particular purposes. For example, the cross section can be oval or rectangular where optical detection of components within a compartment is enhanced by increasing the optical path length or providing a larger optical surface to be viewed. Alternatively, with linear piston motion, a non-circular cross-section can be used to prevent rotation of the piston where its orientation is important.

The device can be constructed with more or less compartments depending on the stringency of the application such as in the sensitivity requirement and the complexity of the overall analytical process required to achieve this.

The detection phase of the analysis can be conducted within a compartment of the device such as by fluorescence whereby the chamber is irradiated by excitation optical energy and fluorescent light is consequently detected, with the detection compartment being constructed of appropriately transparent material or being fabricated with windows.

Although the description of this illustrative embodiment includes the use of lysis reagents for assays involving blood samples, other types of biological samples can be analyzed by the device, including those that do not require cell lysis nor the attendant lysing reagents.

Figure 13:
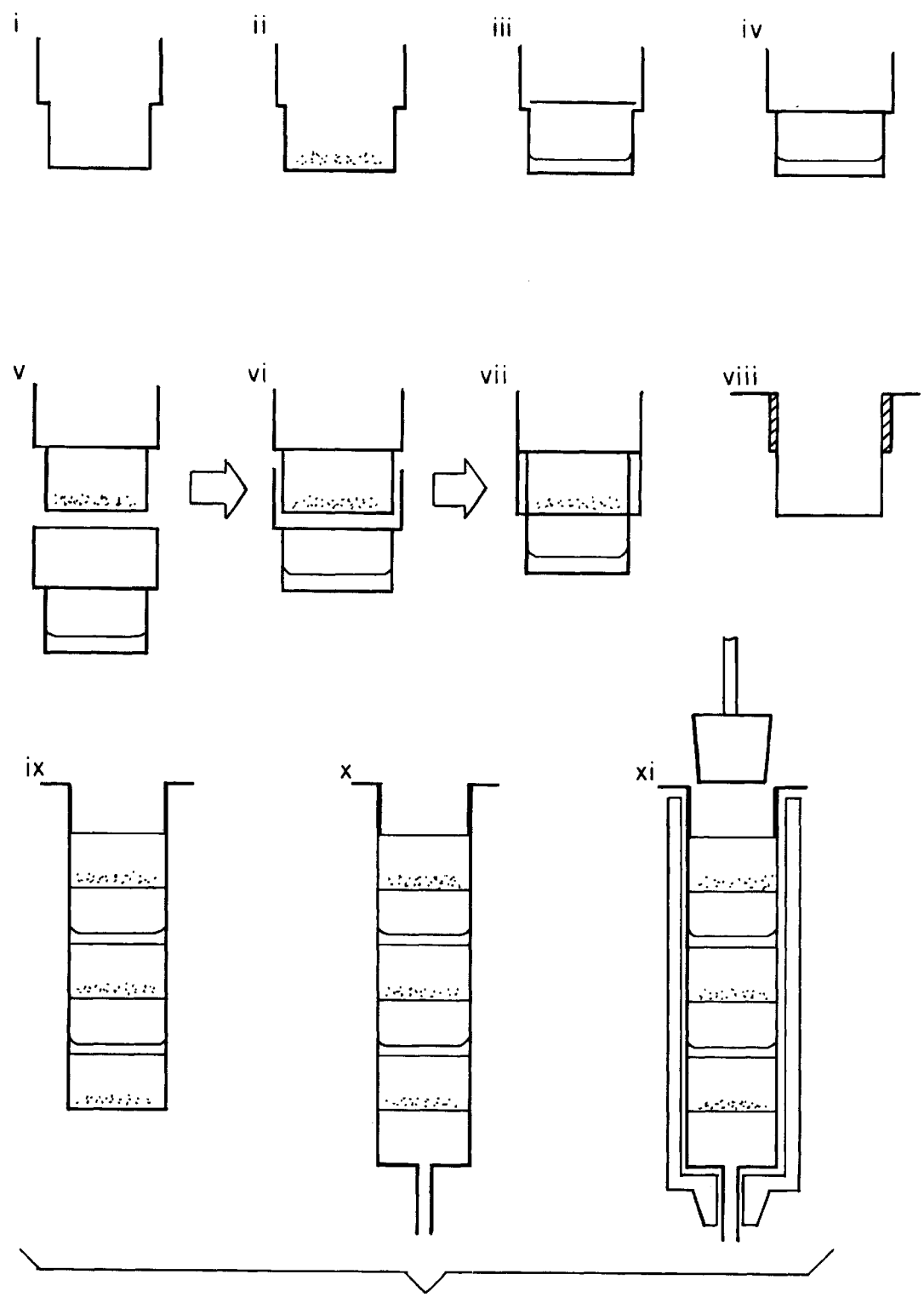
FIG. 13 depicts the stages of construction for piston liners.

FIG. 13 depicts the steps in fabricating the reaction chamber in a particular embodiment. The reaction chamber is fabricated of some material which is benign towards the assays conducted, such as by having a tolerably low level of inhibition to PCR or other enzyme-based assays and/or having a tolerably low surface adsorption of proteins such that alternative uses of the device for immunoassay can be conducted with tolerably low interference in immunoassay based analyses, or that these effects are sufficiently low and/or predictable such that they may be compensated for or numerically corrected for in analyzing the analytical results, and the benign storage of included wet and/or dry reagents for extended periods is required for commercially useful product self lives. The reaction chamber material needs sufficient strength such that it adequately maintains its shape during the analysis but the inter-compartment barriers are able to be ruptured or pierced during the analysis. Also, the material needs to be amenable to welding such as by ultrasonic means or use of adhesives with adequate long-term strength. A wide variety of plastic materials is available with useful properties as is known by those of skill in the art such as mylar for strength and polyproplyene for PCR compatibility. The reaction chamber material may advantageously be layered, such as formed in mylar with an inner polypropylene coating.

Within FIG. 13, illustration (i)depicts in cross-section a reaction chamber element that is about to become part of a complete reaction chamber. There are two cylindrical sections with the upper part having a slightly greater diameter, and the lower part featuring a flat circular bottom to its chamber. Illustrations (ii) depicts how the reaction chamber element can be preloaded with reagents, in this case as dried or lyophilized. Illustration (iii) shows a sealing disk of diameter matching the inner diameter of the upper part is positioned to close the lower unit into a sealed compartment, in this case depicted incompletely fill with liquid content. Illustration (iv) shows the compartment sealed by the disk being, for example, welded or otherwise attached to the circular shoulder at the entrance to the lower unit, such that becomes a complete and sealed compartment, in this case depicted with liquid content. Illustration (v) depicts how two such compartments can be positioned to be joined, and illustration (vi) depicts the lower unit of the upper compartment being inserted into the upper unit of the lower compartment, where the outer diameter of the lower unit closely matches the inner diameter of the upper unit. Illustration (vii) depicts the attachment of the two compartments, by welding or use of adhesives or an adequately tight push fit or by other known means such that both the inner diameters of the two compartments are maintained approximately contiguously across the join. Illustration (viii) depicts a top element to the overall device which features a lip or other feature that can be located against the end of a syringe body or other outer sample collection unit for the overall device, together with a lower unit that can be joined with other compartments as described above. The inner diameter of this top element can be made constant by featuring a thicker wall in its top element such that a liner made with this top element may have a consistent inner diameter. Illustration (ix) depicts a complete device with a top element as above and a lower unit which is a sealed compartment. Illustration (x) depicts an alternate embodiment where the lower unit is open through a formed channel that may, for example, be conducted through the sharp end of a syringe barrel or directed to some other device or purpose such as an external detection chamber or device. Illustration (xi) depicts a complete reaction chamber located within a syringe barrel, where the top element lip is positioned against the open end of the syringe barrel with the piston head inserted into the open end of the lined syringe barrel, and the formed channel is positioned through the sharp end such that, for example, reaction liquid can be conducted to some external device or purpose. To conduct an analysis with this device, the lined syringe is positioned in some mounting means able to hold it while sample is loaded into the top compartment, the piston head is then inserted, the piston is driven progressively downwards (as here depicted) as the various stages of the analysis proceed. Optical detection can be achieved with optical devices and instrumentation well known to those skilled in the art, by positioning the transparent or translucent syringe and liner such that the appropriate compartment can be optically accessed. Alternatively, the reaction mixture may be expelled or extracted from the device syringe liner through the formed channel for external detection by a variety of known means including optical detection, conductivity measurements, etc.

Example 6
Electrophoretically Assisted Gel Separation

Figure 14:
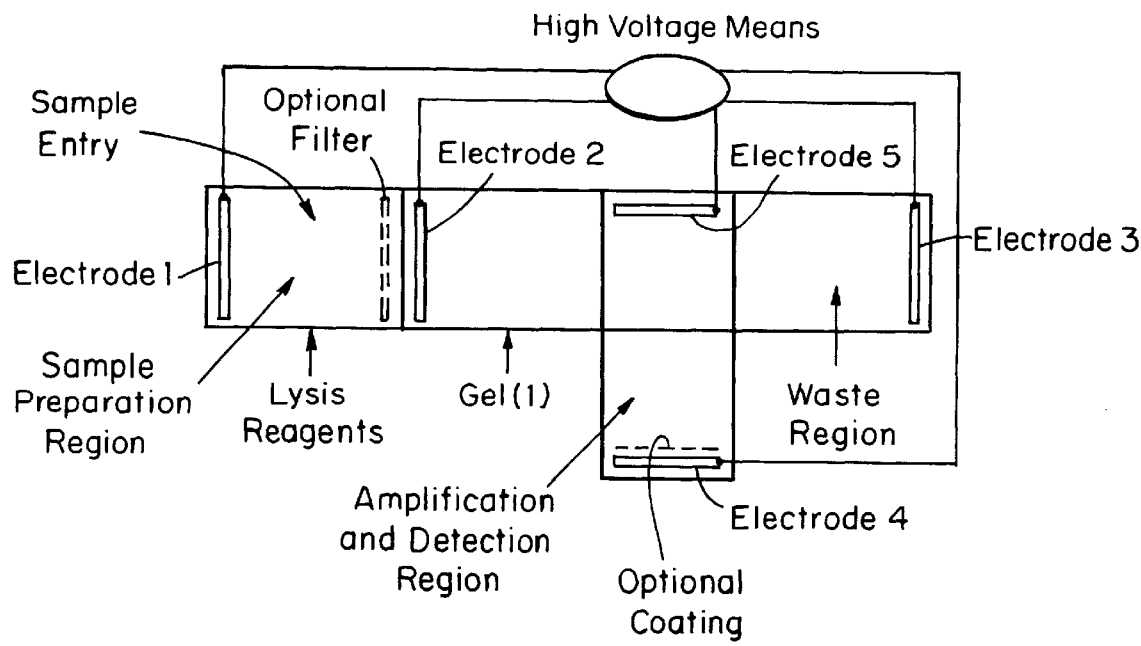
FIG. 14 depicts a schematic representation of electrophoretically assisted amplification analysis.

FIG. 14 depicts an embodiment of the invention where an analytical procedure is performed in a multi-compartment chambered device by electrophoretically assisted gel separation, amplification and detection. A nucleic acid analysis is performed by a sample preparation stage, optionally including cell lysis and neutralization of PCR inhibiting species, followed by separation of components in the resulting mixture by known means involving capturing nucleic acid species in an acrylamide gel, then movement of that part of the gel with said captured species into an amplification chamber where the captured species are liberated and a homogenous amplification procedure is conducted followed by detection of amplified nucleic acid species.

At the commencement of the analysis, the analytical device can be prepared and preconditioned for the following analytical procedures by pre-charging with reagent solutions, re-hydration of gels and other appropriate known means. To commence the analysis a quantity of sample is added to the Sample Preparation Compartment. This contains dissolved reagents which assist with preparing the sample for the pending analysis, including providing the required buffered environment, maintaining the correct pH, lysing cells if appropriate and neutralizing PCR inhibitors that may be present in the applied sample including from lysed cells. The sample remains within this chamber for a period of several minutes for cell lysis to be substantially complete, during which time fluid mixing within this compartment may be achieved by laminar or turbulent flow, diffusion of dissolved components, or with assistance such as from mechanical agitation.

When the sample preparation process is complete, a dc voltage on the order of 0.1 to 10 volts/cm is applied by the High Voltage Means between Electrode 1 and another electrode such as Electrode 3. Such High Voltage Means is a dc voltage source as is readily obtainable from a multitude of commercial sources for laboratory electrophoretic analysis. The application of this voltage causes nucleic acids and other chemical species with similar charges to migrate from the Sample Preparation Compartment into the Gel(l) compartment which is in contact with the contents of the Sample Preparation Compartment either by direct contact or indirectly such as through an appropriate membrane. An optional filter can be positioned such as to restrain, for example, cell debris from impacting the side of the gel and potentially diminishing fluid access. Depending on the dimensions of the compartments involved, an electrophoretic voltage is applied for a time on the order of a minute until the nucleic acid components of interest have sufficiently migrated into Gel(1). As an alternative, the electrophoretic voltage can be applied between Electrode 1 and Electrode 4, but this has the possible disadvantage that chemical species can migrate into the Amplification and Detection Compartment as contaminants.

When sufficient nucleic acid species of interest have migrated into Gel(1). The High Voltage Means is connected between Electrode 2 and Electrode 3 and an appropriate voltage is applied to further migrate chemical species already within Gel(1) and in particular the nucleic acids of interest towards Electrode 3 within Gel 3. Depending on the overall device dimensions and form, a voltage on the order of hundreds of volts is applied between the electrodes for a period on the order of minutes. The Thermolabile Gel 2 is an acrylamide gel which has within its envelope one or more covalently bound nucleic acid probes. These probes are co-polymerized into the gel by known means whereby a length of nucleic acid to be used as a probe is covalently attached to an acrylamide moiety, and the acrylamide moiety is co-polymerized into the gel such that the probe is covalently bonded to the gel. As nucleic acid species derived from the applied sample are electrophoretically driven through Gel 2, those species having complementary sequences to the immobilized probes become attached to said probes, and by this attachment are held in place such that their migration ceases. In situations where it is desired to analyze multiple nucleic acid species in parallel, a set of probes each being complementary to a region of at least one such species can be attached to Gel 2 such that each of the nucleic acids of interest is captured if present in the applied sample. The applied electrophoresis driving voltage is maintained until sufficient quantities of nucleic acids of interest have migrated into Gel 2 and been captured by the immobilized probes. At this point the applied voltage is turned off. As an alternative, the electrophoretic voltage could be applied between Electrode 1 and Electrode 4, but this has the potential disadvantage of additional material migrating from the Sample Preparation Compartment though Gel 1 into Gel 2 and contaminating this nucleic acid capture region. When sufficient sample nucleic acid has been captured by Gel 2, the nucleic acid is transferred into the Amplification and Detection Region. Said transfer can be made by physically moving Gel 2 into this compartment such as by it being pushed by a piston or other mechanical device (not shown) which causes the physical motion. Alternatively, Gel 2 can be physically left in place but the captured nucleic acids from the sample may be caused to migrate into the Amplification and Detection Compartment. This migration may conveniently be arranged by applying an electrophoretic high voltage between Electrode 4 and Electrode 5 causing nucleic acids to migrate towards Electrode 4. The applied voltage is on the order of 100 volts/cm or more sufficient to dehybridize the captured nucleic acids from the immobilized complementary probes. Depending upon the dimensions and shape of the device, this voltage can be applied for relatively short period on the order of a few minutes or less, as the migration rate of liberated nucleic acids will be relatively rapid. Any nucleic acids which migrate sufficiently to actually contact Electrode 4 can be destroyed by so doing, such that an optional coating can be applied to Electrode 4 which permits electrical connection but prevents damage to impinging nucleic acids, such as cellulose dialysis membrane with a molecular weight cutoff of less than 30 kilodaltons. Such coating can be a membrane of known type which passes electrolyte but is impermeable to nucleic acids. The applied electrophoretic voltage is applied until sufficient nucleic acid has migrated from Gel 2 into the Amplification and detection Chamber.

The Amplification and Detection Chamber optionally contains PCR reagents to support a PCR amplification process together with PCR primers appropriate to all the nucleic acid species in the applied sample that it is desired to analyze. These reagents can be preloaded into this compartment, or can be loaded at the commencement of the analysis. As an alternative, the PCR primers can have been previously attached to Gel 2 by the aforementioned mechanism whereby they are hybridized to complementary probes covalently attached to the gel by copolymerized acrydite moieties. PCR amplification is commenced by thermocycling the Amplification and Detection Compartment by known means such as thermal coupling to an external heating/cooling means, directly heating and cooling the compartment such as with peltier elements attached to its walls or boundaries, or by directly heating the liquid therein by applied electromagnetic radiation such radiofrequency or microwave energy or by the application of infrared light. If the sample nucleic acids and optionally the PCR primers were transferred to this compartment by physical transfer of Gel 2 as described above, the material of Gel 2 is a thermolabile gel of known type which dissolves on heating to a temperature approximating to that required for PCR denaturation such as approximately 95 degrees C. Thus, on the initial PCR denaturation cycle, denaturation of the hybridized nucleic acids and optionally the PCR primers released from the gel will occur, such that these species are able to participate in PCR amplification. Thermocycling of the Amplification and Detection Compartment and its components is continued for typically 30 to 40 cycles or until the concentration of amplified nucleic acids has grown to an appropriate level for subsequent detection.

After completion of the amplification process, the amplificate is detected by known means. Such means include optical detection following staining with dyes such as ethidium bromide or other commercially available dyes, or hybridization to nucleic acid probes with sequences complementary with those of amplified nucleic acids where such probes may be fluorescently or enzymatically labeled. If merely a single nucleic acid species from the applied sample is to amplified and detected, a single stain or detectably labeled probe can be used non-specifically. Alternatively, if multiple nucleic acids in the applied sample are of interest to determine the presence of any one or any combination then generic staining or use of multiple labeled probes with the same label will yield the required generic result it any are present. Alternatively, if it is desired to independently detect the presence of more than one nucleic acid species or sequence in the applied sample, then probes with optically distinguishable different labels are used for different nucleic acid species or sequences potentially present in the applied sample. For separate parallel detection, it is particularly advantageous to use beacon probes containing both a fluorophore and quencher whose fluorescence is greatly magnified by being hybridized to a complementary nucleic acid sequence, as can probes may be contained in solution such that their fluorescence may be optically detected if they are so hybridized without the need for removal of non-hybridized probe as would be the case for probes whose non-hybridized form would significantly interfere with optical detection of the hybridized form.

The processes of amplification and detection can be conducted in the same Compartment, which is optically accessible from an optical detection means (not shown). Alternatively, the processes of amplification and detection can be interleaved by detecting the staining of nucleic acid amplificate or the hybridization of label detection probes after each PCR cycle typically during or after each extension phase. As an alternative, the amplificate can be transferred to an external detection compartment (not shown) which is accessible to appropriate detection means.

Although PCR is explicitly referenced as a preferred embodiment other nucleic acid amplification schemes are also included, particularly the use of the ligase chain reaction (LCR), and Cascade amplification.

Figure 15:
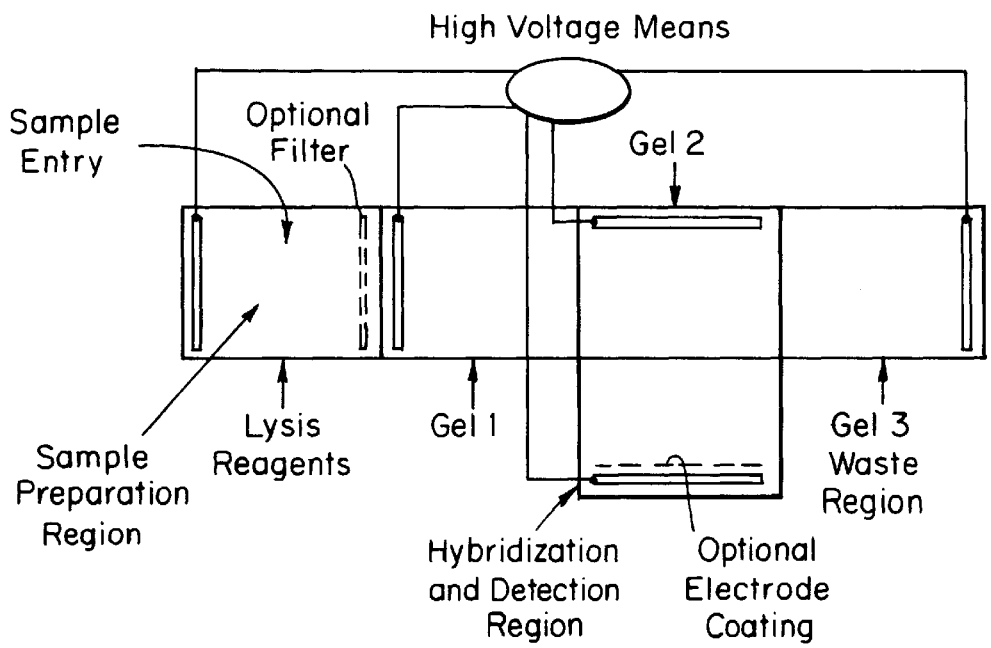
FIG. 15 depicts a schematic representation of electrophoretically assisted hybridization analysis with Gel 2 laterally extended.

Example 7
Detection of a Target Molecule Electrophoretically without the use of Amplification FIG. 15 depicts another embodiment of the invention where an analytical procedure is performed in a device with reaction components being transferred electrophoretically. The component parts of this device, and their method of use, are broadly similar to Example 6 above as depicted by FIG. 14. However, the device illustrated as FIG. 15 conducts analyses by hybridization of nucleic acids in the applied sample without the requirement for amplification. This is a particularly advantageous simplification of the device and its method of use which can be utilized for relatively high concentration of applied nucleic acid samples for which the process of amplification is unnecessary.

The overall analytical sequence is broadly similar to the example above, with sample input and sample preparation optionally including cell lysis in the Sample Preparation Compartment, and electrophoretically induced migration of nucleic acid species between compartments. In this case the applied sample nucleic acids captured on the Gel are moved physically or by electrophoretic migration as above to the Hybridization and Detection Compartment where hybridization or staining are conducted as above followed by detection in this compartment or optionally in a different compartment or external to the device using reagents and detection techniques as described above.

Figure 16:
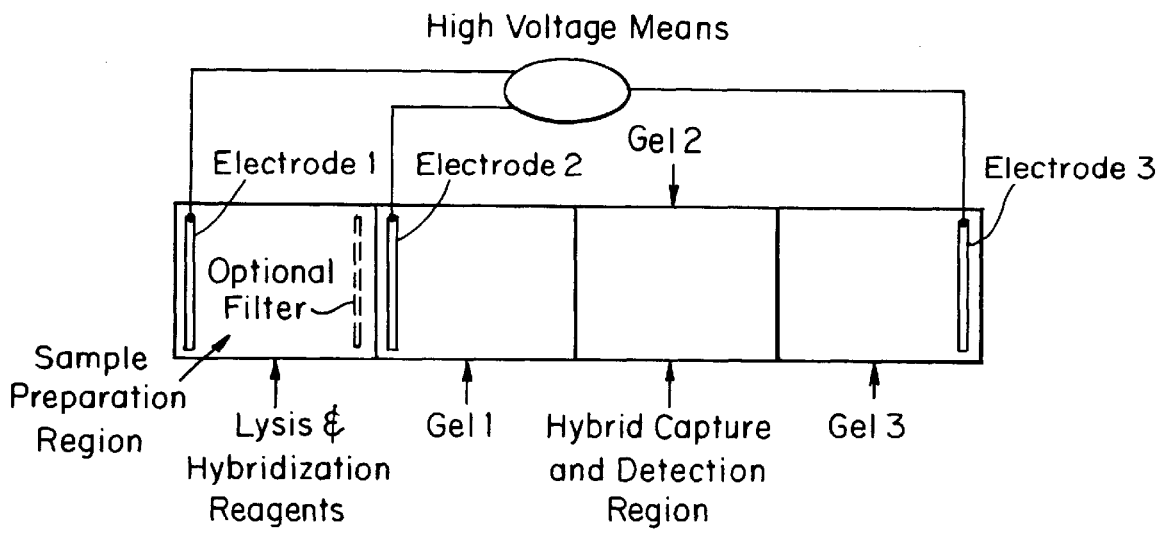
FIG. 16 depicts a schematic representation of electrophoretically assisted hybridization analysis with Gel 2 in place.

Example 8
Electrophoretic Detection of Nucleic Acid Target Molecules without Amplification FIG. 16 depicts a further embodiment of the invention where an analytical procedure is performed in a device with reaction components being transferred electrophoretically. The component parts of this device, and their method of use are broadly similar to Examples 6 and 7 depicted by FIGS. 14 and 15 above. However, the device illustrated as FIG. 16 conducts analyses by hybridization of nucleic acids without prior amplification and detects the hybridized target nucleic species at their capture site on a gel with a simpler device without the requirement for a separate detection compartment.

The overall analytical sequence is essentially similar to the examples above, with sample input and sample preparation optionally including cell lysis in the Sample Preparation Compartment, and electrophoretically induced migration of nucleic acid species between compartments. In this case, one or more nucleic acids of interest within the applied sample are hybridized to a detectably labeled probe within the Sample Preparation Compartment using reagents provided for this purpose within this compartment either as a solution or by the applied sample dissolving dried or lyophilized reagents. Alternatively, these reagents can be added to this compartment during the initial stage of the analysis such as by entry though the same or similar means as entry of the applied sample. The applied sample and provided reagents are mixed and permitted to react for a time period on the order of tens of seconds or minutes for the lysis and hybridization processes to be sufficiently complete. Optionally, this process may be assisted by heating the sample and reagent mixture in order to assist with denaturation of the target nucleic acids and their hybridization to probes.

When the target nucleic acids in the sample, being those nucleic acids of interest for which hybridization probes have been provided, have been hybridized as above, electrophoretic voltages are applied to migrate the nucleic acid species into the gel. Initially, a voltage on the order of 0.1 to 10 of volts/cm is applied for a period on the order of tens of seconds to 120 minutes between Electrode 1 and Electrode 3 to cause migration of the hybridized nucleic acids into some area of the set of gels. When sufficient time has elapsed for the hybridized target nucleic acids to have migrated into a gel, the voltages are reapplied to Electrode 2 and Electrode 3 to continue the migration of hybridized target nucleic acid towards Electrode 3. As the target nucleic acids migrate through Gel 2, they encounter complementary capture probes that are immobilized to the gel such as by covalent linkage with acrylamide moieties that are co-polymerized into an acrylamide gel. These capture probes are complementary to a different part of the target nucleic acid in order the time target nucleic acid can be simultaneously hybridized to both types of probe. If the applied sample contains one or more target nucleic acids having sequences complementary to those of the capture probes, said target nucleic acid species become captured on Gel 2 at this point, whereas other nucleic acid species will continue to migrate through and past the capture compartment into another area of the device such as Gel 3 and will ultimately encounter Electrode 3. The electrophoretic voltage is applied for sufficient time for all hybridized target nucleic acids to have reached the capture compartment on Gel 2 and for other nucleic acids, particularly non-hybridized detectable labeled nucleic acid probes, to have migrated through and away from the capture compartment. This electrophoretic migration phase can be continued for sufficient time for other chemical species potentially interfering with the analysis to also have migrated distinct from the capture compartment. Depending on the device dimension and format and the actual value of the applied electrophoretic voltage, this time can range from the order of tens of seconds to minutes. As a simpler alternative, this phase of electrophoretic migration can be induced by continuing to apply the voltage between Electrode 1 and Electrode 2, however this can cause interfering chemical species to continue to enter Gel 1 and potentially interfere with the analysis.

When all or a sufficient number of the hybridized target nucleic acids have passed into the capture compartment of Gel 2 and been captured, while the other interfering species particularly unhybridized labeled probes have migrated past the capture compartment, the electrophoretic migration can be terminated. The one or more target nucleic acids can then be detected by their presence in the capture zone. Such detection can be accomplished by a variety of known means including the use of fluorescent probes, or enzyme probes operating with some substrate present as a reagent in solution such as a fluorogenic substrate or a chemiluminescent substrate.

Multiple nucleic acids species can be hybridized, captured and distinguishably detected by a variety of means. For instance, different fluorophores can be used with different labeled probes such that intermixed captured and labeled nucleic acids can be optically distinguished such as by selective optical filtration. Alternatively, the capture zone can be organized with spatially distinct sub-compartments each containing only one or a lesser numbers of capture probes, such that the various target nucleic acids are capture in different sub-compartments and can be optically distinguished by an optical scanning process or by optically imaging the optically detectable signals onto a liner or area sensitive optical detector such as a photomultiplier or charge coupled device.

As an alternative embodiment, the target nucleic acids can be captured on the gel by hybridization to the immobilized capture probes without previously being hybridized to labeled probes for detection. The labeled probes can then me added after the capture process such from a solution addition means (not shown) such that hybridization of labeled detection probes occurs after target capture on the gel. Residual non-hybridized labeled probe can then be removed from the capture/detection area before detection, by means such as electrophoresis. Alternatively, if the labeled probes are of a form that will not give a detectable signal unless hybridized, or which give distinguishably different signals in their non-hybridized and hybridized forms, there can be no need to remove unhybridized labeled probes before detection.

As a further option, and simplification of the device, either or both of Gel 1 and Gel 3 can be deleted such that a single gel is used, with all or part serving as the capture compartment, and optionally only a single phase of electrophoretic migration being used.

Example 9
Solution Assay Using Beacon Probes

Figure 17:
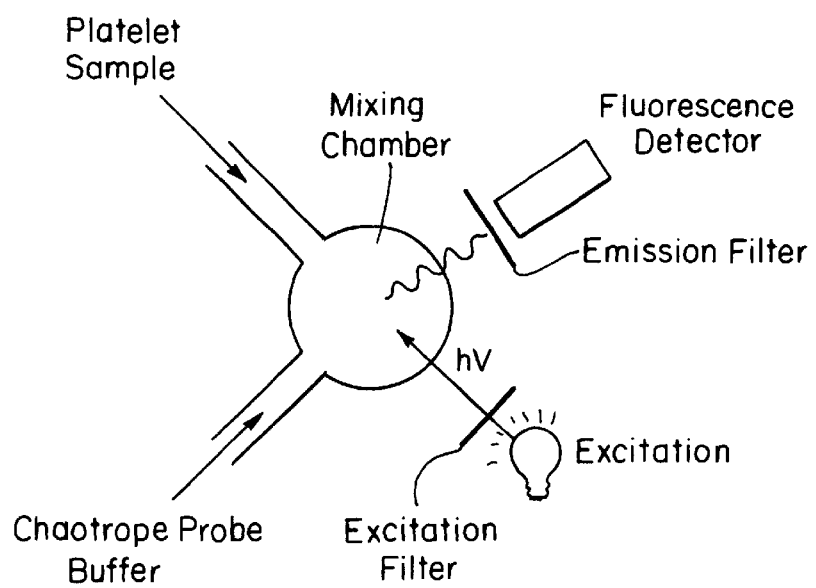
FIG. 17 depicts a schematic representation of a device used for beacon probe and FRET probe assays.

The object of the assay is to determine whether a platelet concentrate is contaminated with bacteria. This example can be extended to the examination of other biological samples. (See. FIG. 17). Bacterial growth is a major concern for platelet transfusion, since platelets must be stored at room temperature.

The beacon probe is designed to hybridize with a conserved eubacterial 16S rRNA sequence: EDANS-5'-gcgagtgcTAAACCACATGCTCCACCGCTTGTGgcactcgc-3'-DABCYL, [SEQ. ID No. 1] wherein EDANS is the fluorophore 5-(2'aminoethyl)aminonaphthalene-1-sulfonic acid and DABCYL is the quencher 4-(4'-dimethylaminophenylazo)benzoic acid. The probe sequences to 16S rRNA are shown in upper case which is complementary to E.coli's 16S rRNA positions 933–957 (Genbank accession No. M24996). Complementary arm sequences shown in lower case hybridize to form the duplex hairpin stem of the beacon probe in the absence of bacterial target RNA. The synthesis of this beacon probe can be performed as that described by Tyagi and Kramer (*Nature Biotechnology*, 14:303–308 (1996)).

To perform the analysis, a measured sample of platelet concentrate is added to a mixing chamber that contains lyophilized lysozyme (Sigma Chemical catalog # L6876 (1998)) and mutanolysin (Sigma Chemical catalog # M9901 (1998)), to digest bacterial cell walls. The sample is mixed to re-dissolve the enzymes, and the lysis mixture is incubated for 5 to 10 minutes at 25–37° C. Preferably, the sample volume is from 0.1 to 1 mL in volume. The final concentrations of lysozyme and mutanolysin in the sample fall in the range of 2–5 mg/mL and 100–200 units/mL. Five volumes of chaotrope probe buffer (6 M guanidine thiocyanate (GuSCN), 0.1 M Tris-HCl, pH 8.0, 2 mM EDTA and beacon probe) are added to the enzyme-digested sample, and the sample is mixed to complete lysis and initiate hybridization of the beacon probe. In addition to the chaotrope reagents, the chaotrope buffer solution also contains the beacon probe, preferably at a concentration between 0.01 and 10 $\mu$M. The reaction is incubated for another 5 to 10 minute period at 25–37° C. to allow for hybridization.

To assess hybridization of the beacon probe, the reaction is monitored for fluorescence using excitation at 366 nm and emission at 490 nm. Fluorescence signals that exceed the value of control reactions (containing no platelet sample) by a certain margin indicates the presence of bacterial rRNA in the sample, suggesting that the platelet sample is contaminated. The margin of excess fluorescence necessary to score a platelet sample contaminated should be determined by a clinical trial.

Depending on the room temperature in the testing laboratory, the final reaction mixture may be too destabilizing to allow stable formation of the stem duplex due to the high concentration of GuSCN, which lowers the melting temperature of nucleic acid duplexes. (Thompson and Gillespie, *Anal. Biochemistry*, 163:281–291 (1987)). Two actions can be taken to lower the background. First, the entire reaction volume can be diluted 1:1 (vol:vol) with water before fluorescence measurement. This lowers chaotrope concentration, thereby raising the melting temperature of the stem duplex. If this is insufficient, then $MgCl_2$ can be added to a final free concentration of 1 mM (3 mM total concentration, assuming quantitative binding of $Mg^{++}$ by EDTA). Divalent ions greatly stabilize hairpin duplexes. Preferably, the $Mg^{++}$ is added after hybridization to the target RNA since it also will stabilize RNA secondary structure and interfere with probe hybridization.

Example 10
Solution Hybridization Assay Using FRET Probes.

The object of this assay is to determine whether a platelet concentrate is contaminated with bacteria. This assay can also be extended to the detection of a target molecule in a biological sample. (See FIG. 17).

The design of FRET probes is described by Mergny et al., *Nucleic Acid Research*, 22:920–928 (1994). Essentially, the strategy is to design nucleic acid probes that will hybridize to adjacent compartments of the target polynucleotide. The two probes are labeled such that when hybridized to the target polynucleotide, the donor and acceptor fluorophore are close enough to allow fluorescence resonance energy transfer.

In this example, the two probes are designed to hybridize to a conserved sequence of eubacterial 16S rRNA. The donor probe is: 5'-(Fluorescin)-cgaattaaaccacatgctccac-3', [SEQ ID NO. 2] which complementary to positions 941–962 of *E.coli* 16S rRNA (Genbank accession No. M24996). The acceptor probe is: 5'-gaccaggtaaggttcttcgcgttg-(Rhodamine B)-3', [SEQ ID NO. 3] which is complementary to positions 966–989 of *E.coli* 16S rRNA (Genbank accession No. M24996).

A measured sample of platelet concentrate is added to a mixing chamber that contains lyophilized lysozyme (Sigma Chemical catalog # L6876) and mutanolysin (Sigma Chemical catalog # M9901), to digest bacterial cell walls. The sample is mixed to re-dissolve the enzymes, and the lysis mixture is incubated for 5–10 minutes a 25–37° C. Preferably, the sample volume is from 0.1 to 1 mL in volume. Preferably the final concentrations of lysozyme and mutanolysin in the sample fall in the range of 2–5 mg/mL and 100–200 units/mL, respectively. Five volumes (the original volume of platelet concentrate added to the mixing chamber is defined as one volume) of chaotrope probe buffer (6 M guanidine thiocyanate [GuSCN], 0.1 M Tris HCL, pH 8.0, 10 mM EDTA, and beacon probe) are added to the enzyme-digested sample, and the sample is mixed to complete lysis and initiate hybridization of the beacon probe. In addition to the chaotrope reagents, the chaotrope probe buffer solution also contains the FRET probes, preferably each one present at a concentration between 0.01 $\mu$M and 100 $\mu$M, and more preferably between 0.01 $\mu$M and 10 $\mu$M. The reaction is incubated for another 5–10 minute period at 25–37° C., to allow hybridization.

To assess hybridization of the FRET probes, fluorescence of the mixture is measured using excitation at 485 nm and emission at 590 nm. Fluorescence signals that exceed the value of control reactions (containing no platelet sample) by a certain margin indicated the presence of bacterial rRNA in the sample, and suggest that the platelet sample is contaminated. The margin of excess fluorescence necessary to score a platelet sample is contaminated should be determined by a clinical trial.

Example 11
Gel Hybridization Assay for Bacterial Contamination in Whole Blood

Figure 18A:
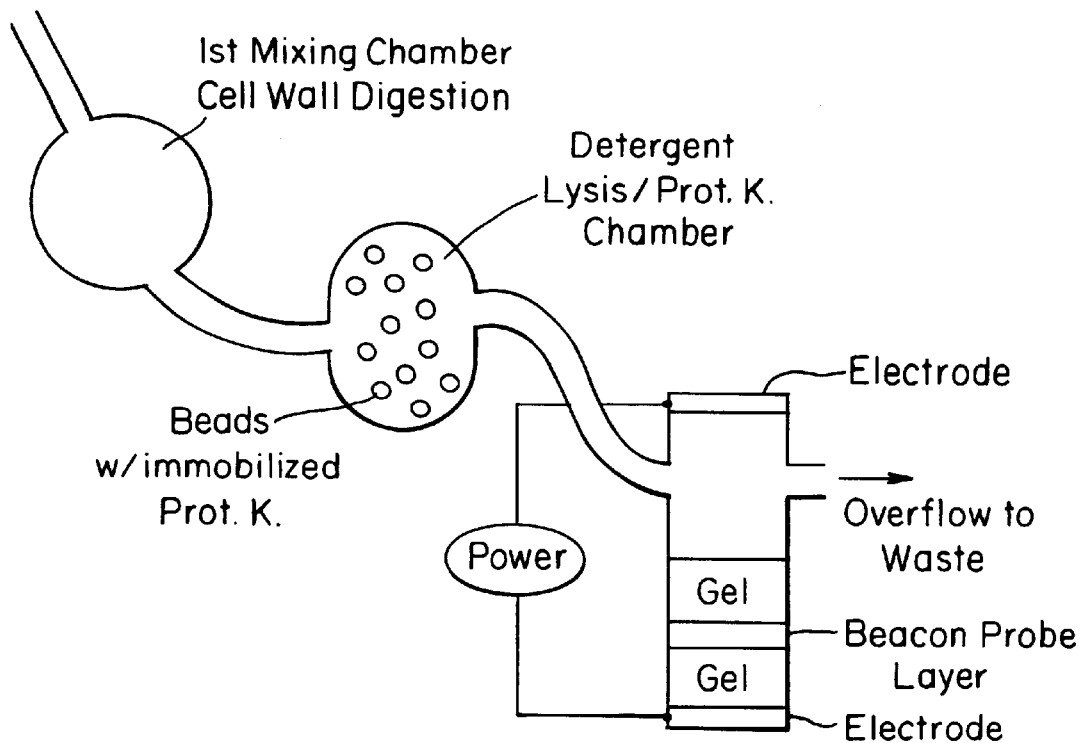
FIG. 18A and FIG. 18B depict a schematic representation of a device used for a gel hybridization assay.
Figure 18B:
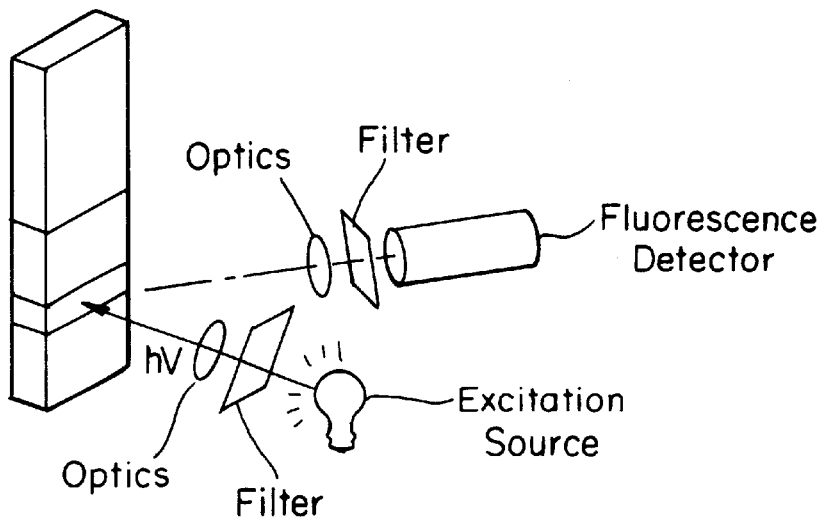

A measure sample of blood from the bag is added to a mixing chamber that contains lyophilized lysozyme (Sigma Chemical catalog # L6876) and mutanolysin (Sigma Chemical catalog # M9901), to digest bacterial cell walls. The sample is mixed to re-dissolve the enzymes, and the lysis mixture is incubated for 5–10 minutes a 25–37° C. (See FIG. 18.) Preferably the sample volume is from 0.1 to 1 mL is volume; more preferably 0.1 mL. Preferably, the final concentrations of lysozyme and mutanolysin in the sample fall in the range of 2–5 mg/mL and 100–200 units/mL, respectively.

The digested sample is lysed and transferred into a second chamber which contains five volumes (the original volume of platelet concentrate added to the mixing chamber is defined as on volume) of detergent buffer (0.1 M Tris HCL pH 8.0, 0.5% SDS, 5 mM EDTA) and 100 units of proteinase K immobilized on beads (Amersham Pharmacia Biotech). The sample mixed and incubated for 5–20 minutes at 37°–60° C.

The lysed sample is then transferred into the sample compartment of a 4% polyacrylamide electrophoresis gel (29:1; weight ratio monomer acrylamide:bisacrylamide). The gel is composed of three layers: the top and bottom layers contain unmodified polyacrylamide. The center layer that contains an immobilized beacon probe that is complementary to a conserved region of eubacterial 16S rRNA. The beacon probe described in Example 9 above can be used, with the exception that an acrylamide phorsphoramidite (Acrydite™ phosphoramidite, Mosaic Technologies, Boston, Mass.). For immobilization, the acrylamide-modified probe is mixed with the monomer/bis acrylamide solution and copolymerized into the polyacrylamide layer during gel casting. Preferably, the concentration of beacon probe in the probe gel layer is between 0.1–100 $\mu$M; and more preferably between 1 and 10 $\mu$M. The sample is subjected to electrophoresis in this gel, at fields between 1–10 V/cm. The gel buffer is 0.1 M Tris-HCL, 2 mM EDTA, 0.1% SDS. After electrophoresis the fluorescence of the beacon probe layer is measured using excitation at 366 nm and emission at 490 nm. If present, rRNA fragments complementary to the immobilized beacon will hybridize to the beacon probe and release the DABCYL—mediated quenching of EDANS fluorescence. Fluorescence signals that exceed the value of control reactions (containing no platelet sample) by a certain margin indicate the presence of bacterial rRNA in the sample, and suggest that the plate sample is contaminated. The margin of excess fluorescence necessary to score a platelet sample contaminated should be determined by a clinical trial.

Figure 19A:
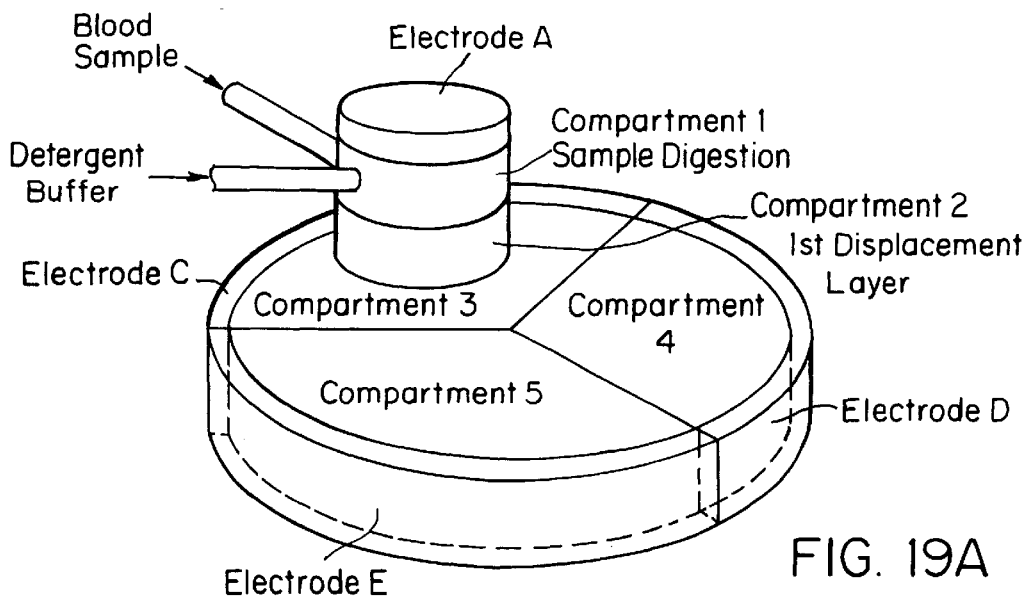
FIG. 19a depicts a schematic representation of a device used for analyzing nucleic acid samples.
Figure 19B:
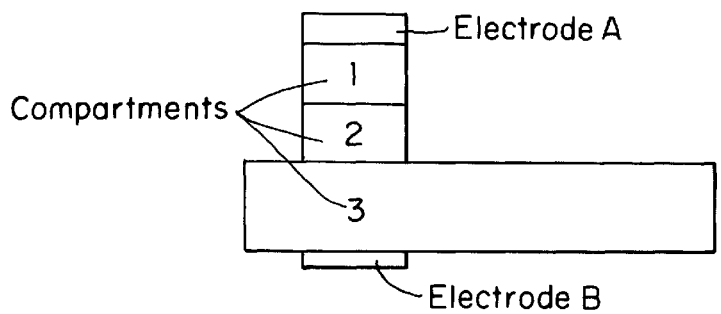
FIG. 19b depicts a schematic representation of the compartments contained within the device.
Figure 19C:
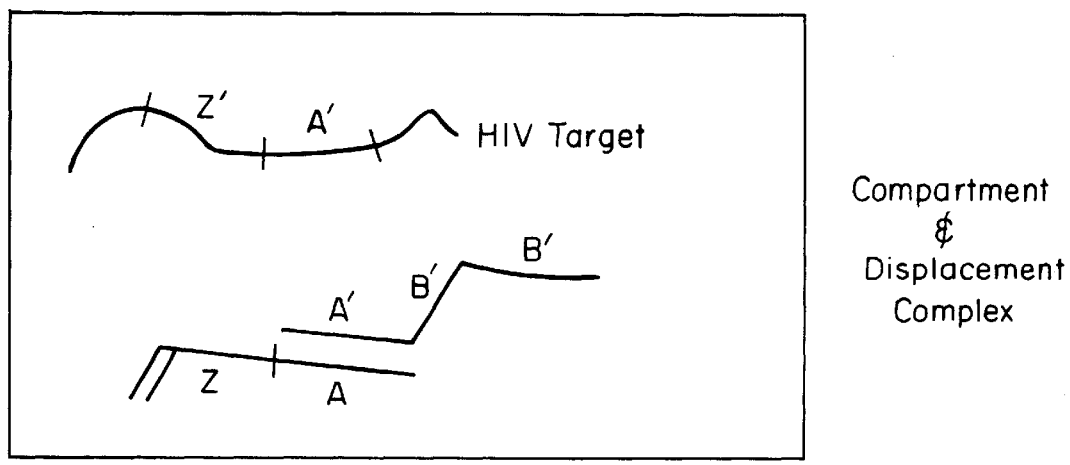
FIG. 19c depicts a schematic representation of a compartment housing a displacement complex.

Example 12
Assay for HIV using recursive multiple sequential strand displacement The assay uses a five compartment electrophoresis device as shown in FIG. 19. Compartment 1 is dedicated for sample preparation. Compartments 2–5 contain displacement probe complexes. Preferably, the gel is composed of 3–5% polyacrylamide (29:1; weight ratio monomer:bis acrylamide) containing buffer of 0.1 M Tris acetate pH 8.0, 2% SDS mM EDTA. Other buffers can also be used.

At the start of the assay, compartment one contains lysophilized proteinase K. Detergent buffer (0.1 M Tris acetate pH 8.0, 2% SDS, 5 mM EDTA) is added to the compartment and mixed to resuspend the proteinase K. The final concentration of proteinase K is preferably in the range of 50–500 $\mu$g/mL, more preferably 50–200 $\mu$g/mL. After protein resuspension, a measured amount of whole blood is added to the compartment. Preferably the volume of blood added ranges from 0.01 to 1 mL in volume; more preferably 0.01 to 0.1 mL of blood is used. The sample is mixed and incubated for 5–30 minutes at 37°–60° C. to liberate viral RNA from the blood.

After proteinase digestion, the sample nucleic acid mixture are electrophoresed into compartment(2) using electrode combination (A). Preferably, electrophoresis is carried out at field strengths between 0.1 –10 V/cm, more preferably between 1–5 V/cm; and temperatures between 25°–50° C., more preferably between 25° C. and 40° C.

Compartments (2 through 5) contain a displacement probe complex immobilized on the polyacrylamide gel matrices that fill the compartments. For the present example, the specific sequences of the HIV target RNA and the displacement complexes are shown in Table 1.

Compartments 2–5 are formed by copolymerizing separate sections of polyacrylamide gel each with a specific displacement complex. The gel sections are separated from the electrodes A–E by size-selective membranes that allow current flow but prevent passage of the displaced nucleic acids. An example of such membrane is a cellulose-based dialysis membrane of molecular weight cutoff<3000 daltons. Other materials of equivalent porosity and permeability may also be used.

If present, HIV RNA will hybridize to single stranded regions within the displacement complex of compartment 2 and displace nucleic acid A'B'B' (Table 1) from the displacement complex by homologous strand exchange.

The displaced nucleic acid A'B'B' in compartment 2 is moved into compartment 3 by electophoresis using electrodes C and D. In compartment 3, nucleic acid A'B'B' displaces nucleic acid B'C'C' from the displacement complex immobilized therein.

And so on around the circuit recursively until high amplification is achieved.

Detection of amplification can be carried out by tagging the displaceable nucleic acid of one compartment with a fluorescent tag, and monitoring the increase in fluorescence in the next compartment. For example, if the displaceable nucleic acid of compartment three (C'A'A') is tagged with a fluorescein fluorescence in compartment four. Other strategies using FRET fluorophores or absorbance changes in the changes will also be apparent to those skilled in the art.

TABLE 1

```
Target of HIV RNA in gag region:
HIV-1 target sequence positions 911-974 of HIV-1 HXB2 isolate Genbank accesion M38432.
```

```
5'-...gggacatcaagcagccatgcaaatgttaaaa gagaccatcaatgaggaagctgcagaatgggat...-3'           [SEQ ID NO. 4]
            A                                         B Compartment 1 (where target comes in)
5'Ac-cBcA 5'-Acrydite-atcccattctgcagcttcctcattgatggtctc ttttaacatttgcatggctgcttgatgtccc-3'         [SEQ ID NO. 5]
              B'                                          A'

BFF oligo:

5'-gagaccatcaatgaggaagctgcagaatgggat AATGGAGAAAGACGGAGAGC                                [SEQ ID NO. 6]
                 B                                F

AATGGAGAAAGACGGAGAGC-3'
         F

Compartment 2 (First amplification compartment)
5'-FEE-3'

5'-AATGGAGAAAGACGGAGAGC CAAAAACGATAAACCAACCA                                             [SEQ ID NO. 7]
          F                     E

CAAAAACGATAAACCAACCA-3'
         E
5'-Ac-cFcFcB-3'

5'-Acrydite-GCTCTCCGTCTTTCTCCATT GCTCTCCGTCTTTCTCCATT                                    [SEQ ID NO. 8]
                 cF                      cF atcccattctgcagcttcctcattgatggtctc-3'
                cB Compartment 3 (Second amplification compartment)
5'-Fluorescein-EBB-3'

5'-F-CAAAAACGATAAACCAACCA gagaccatcaatgaggaagctgcagaatgggat                              [SEQ ID NO. 9]
            E                            B gagaccatcaatgaggaagctgcagaatgggat-3'
                B
5'-Ac-cEcEcF-3'

5'-Acrydite-TGGTTGGTTTATCGTTTTTG TGGTTGGTTTATCGTTTTTGGCTCTCCGTCTTTCTCCATT-3'             [SEQ ID NO. 10]
                 cE                     cE GCTCTCCGTCTTTCTCCATT-3'
         cF Compartment 4 (Third amplification compartment)
5'-BFF-3'

5'-gagaccatcaatgaggaagctgcagaatgggat AATGGAGAAAGACGGAGAGC                                [SEQ ID NO. 11]
                 B                                F

AATGGAGAAAGACGGAGAGC-3'
         F

5'-Ac-cBcBcD-3'

5'Acrydite-atcccattctgcagcttcctcattgatggtctc atcccattctgcagcttcctcattgatggtctc           [SEQ ID NO. 12]
                    cB                                      cB TGGTTGGTTTATCGTTTTTG-3'
         cE
```

Example 13
Solution PCR with Beacon Probe Detection

This example concerns the screening of a biological sample for the presence of HIV-1. The sample, preferably between 10–200 µL, more preferably from 50–100 µL is mixed with four volumes of a mixture containing agarose beads comprising immobilized proteinase K (Sigma #P9290, 200 µL pre-swollen beads) in 100 mM Tris-HCl pH 8.3, 0.6% SDS, 10 mM EDTA. The sample is digested for 10–30 minutes, preferably at a temperature between 30–70° C., more preferably between 45–55° C. Preferably the bead/sample slurry is mixed during digestion. At the end of the digestion period, the sample mixture is loaded into the sample loading chamber of a hybrigel. Optionally, the digestion compartment can also serve as the sample loading compartment.

The hybrigel, for sample preparation, is composed of three sections. (See, FIGS. 14–16). The upper and lower sections are composed of 0.5%–1% agarose, more preferably 0.7%–1%. The middle section of the gel is a composite agarose-polyacrylamide gel, containing copolymerized 5'-Acrydite capture probe (5'-Acrydite- CCT GGT GCA ATA GGC CCT GCA TGC ACT GGA TGC AC -3', complementary to sequence 1439–1473 [SEQ ID No. 13]). The preferred concentration range for the capture probe in the gel is between 1–100 µM, more preferably between 5–10 µM. The preferred agarose concentration range of the middle layer is 0.5%–1%, more preferably 0.7%–1%, and the preferred concentration, of polyacrylamide is 2–3% (weight/volume). Preferably, no bisacrylamide is used so that the polyacrylamide component of the gel is a simple linear copolymer without crosslinking. Preferably, the agarose component of the middle layer is of the low gelling/melting temperature variety, equivalent to the FMC product, Sea-Plaque™. The gel buffer is 100 mM Tris-acetate, pH 8.0, 2 mM EDTA, 0.1% SDS.

The middle layer of the gel is cast within a sliding member or cassette which allows the middle layer to be transferred to the amplification compartment following electrophoresis. Optionally, the middle layer could be separated from the upper and lower gels by porous material or mesh that would facilitate transfer of the layer to the amplification chamber but still allow flow of molecules and electrical current during sample purification.

The gel can have a circular, oval, or rectangular cross section. In one embodiment, the gel layers have a tubular shape with a circular cross section. Approximate dimensions for the upper gel layer are 5 mm diameter by 5 mm height. The middle layer should be small in order to perturb the amplification conditions minimally. Approximate dimensions for the middle layer are 5 mm diameter by 1 mm height. The lower gel layer should be somewhat larger to provide additional buffering capacity for the electrophoresis step. Approximate dimensions for the lower layer are 5 mm diameter by 10–20 mm height.

Electrodes are placed in the top of the sample compartment and at the bottom of the lower gel layer. Preferably electrophoresis is carried out a 1–10 V/cm for 10–60 minutes, more preferably about 10–30 minutes. The time of electrophoresis will depend on the target size.

After electrophoresis, the middle chamber of the gel, now containing the captured RNA target molecules is moved into the amplification compartment. The concentrations of buffers and reactants are adjusted so that the final concentration of the reaction chamber, including the volume and buffer composition of the middle gel layer, is as given in Kwok and Sninsky, 1993, (See, "Diagnostic Molecular Microbiology: Principles and Applications" eds. Persing, D. H. et al. American Society for Microbiology, Washington, D.C.), with the exception that the beacon probe is included in the reaction at a final concentration of 0.2–0.5 µM. The beacon probe that is used in this example is: EDANS-5'gcg agt gc ATC CCA TTC TGC AGC TTC CTC ATT GAT GGT CTC gca ctc gc-3'-DABCYL, wherein the upper case is complementary to position 1403–1435 of HIV-1 target and the lower case forms the stem duplex of the beacon. Cycling is carried out as described by Kwok and Sninsky. The primers that are employed in this specific example are: Primer SK462: 5'-agt tgg agg aca tca agc age cat gca aat-3' (positions 1366–1395) [SEQ ID No. 14]; Primer SK43: 5'-tgc tat gtc agt tcc cct tgg ttc tct-3' (complementary to 1 481–1507) [SEQ ID No. 15]. All sequences are based on the gag gene of HIV-1 from isolated HIVSF-2 (Genbank Accession #KO2007).

Prior to the commencement of the amplification step, the RNA target molecule is reverse transcribed to form DNA. The methods and reagents for RNA PCR are commercially available, for example, from PE Applied Biosystems (RNA PCR Kit, catalog no. N808–0069, Foster City, Calif.).

At the end of thermal cycling, the reaction is held at 95–100° C. for 2–5 minutes and then rapidly cooled to 37° C. Fluorescence is measured using excitation at 336 nm and emission at 490 nm. If the fluorescence measured exceeds a certain threshold value with respect to controls performed without sample, then the sample contained a detectable level of HIV-1 RNA. The value of the threshold and acceptable limits for controls and variation in the assay must be determined by a clinical trial.

EQUIVALENTS

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A cylindrical device for detecting the presence, or absence, of a target molecule in a biological sample contained in a sample collection unit, the device comprising a biocompatible attachment and at least one reaction chamber, wherein the reaction chamber comprises at least one breakable barrier and at least one compartment containing a primer or probe for detecting the presence, or absence, of the target molecule, and further comprising within a cylindrical apparatus capable of circular rotation about a central axis, wherein the apparatus comprises a piston or plunger capable of ingress or egress through the at least one compartment.

2. The device of claim 1, wherein the device is reversibly attached to the sample collection unit.

3. The device of any one of claims 1, or 2, wherein the biological sample enters the reaction chamber through a breakable barrier.

4. The device of claim 1, wherein the apparatus comprises a plunger apparatus.

5. The device of claim 1, wherein a compartment is coated with an electrophoretic media.

6. The device of claim 1, wherein the media is acrylamide.

7. The device of claim 1, wherein a probe is immobilized in the acrylamide media.

8. The device of claim 1, wherein the apparatus is a piston.

9. The device of claim 1, wherein the piston or plunger is threaded.

10. The device of claim 4, wherein the plunger is threaded.

11. The device of claim 7, wherein the piston is threaded.

12. The device of claim 3, wherein the sample is blood.

13. The device of claim 3, wherein the target molecule is a molecule originating from a member selected from the group consisting of a bacteria, a virus, a fungus, a parasite and a biomolecule endogenous to the host from which the sample was obtained.

14. The device of claim 3, wherein the primer is a nucleic acid.

15. The device of claim 3, wherein the probe is selected from the group consisting of a nucleic acid, a protein and a polypeptide.

16. The device of claim 3, wherein the inner surface of a compartment is coated with at least one reagent.

17. The device of claim 3, wherein the reaction chamber comprises multiple compartments.

18. The device of claim 12, wherein the sample collection unit is a blood bag.

19. The device of claim 13, wherein the target molecule is a nucleic acid.

20. The device of claim 13, wherein the target molecule is a protein or polypeptide.

21. The device of claim 15, wherein the protein or polypeptide is an antibody or an antibody fragment.

22. The device of claim 17, wherein the compartments are adjacent and separated by a breakable barrier.

23. The device of claim 17, wherein the apparatus facilitates the movement of sample and/or reagent from one compartment to an adjacent compartment, and wherein the apparatus has at least one analytical surface.

24. The device of claim 17, wherein at least one compartment contains a reagent selected from the group consisting of a cell lysis reagent, an amplification reagent, an amplification inhibitor inactivation regent, a microbiological vital stain reagent and a labeling reagent.

25. The device of claim 21, wherein the probe is detectably labeled.

26. The device of claim 22, wherein the breakable barrier is a membrane.

27. A cylindrical device for detecting the presence, or absence, of a target molecule in a biological fluid contained in a sample collection unit, the device comprising a biocompatible attachment and at least one reaction chamber, wherein the reaction chamber comprises at least one breakable barrier and at least one compartment containing an amplification primer to assist in detecting the presence, or absence, of the target molecule, and further comprising within a cylindrical apparatus capable of circular, rotation about a central axis, wherein the apparatus comprises a piston or plunger capable of ingress or egress through the at least one compartment.

28. The device of claim 27, wherein the device is reversibly attached to the sample collection unit.

29. The device of claim 27, wherein the amplification primer is used in an amplification method selected from the group consisting of polymerase chain reaction, cascade amplification, bridge amplification and ligase chain reaction.

30. The method of claim 29, wherein the primer is immobilized on a solid support.

31. A cylindrical device for detecting the presence, or absence, of a target molecule in a biological fluid contained in a sample collection unit, the device comprising a biocompatible attachment and at least one reaction chamber, wherein the reaction chamber comprises at least one breakable barrier and at least one compartment containing a probe for detecting the presence, or absence, of the target molecule, and further comprising within a cylindrical apparatus capable of circular rotation about a central axis, wherein the apparatus comprises a piston or plunger capable of ingress or egress through the at least one compartment.

32. The device of claim 31, wherein the device is attached to the sample collection unit.

33. The device of claim 31, wherein a compartment is coated with an electrophoretic media.

34. The device of claim 33, wherein the media is acrylimide.

35. The device of claim 34, wherein a probe is immobilized in the acrylimide media.

* * * * *

SEQUENCE LISTING

```
<160> NUMBER OF SEQ ID NOS: 15

<210> SEQ ID NO 1
<211> LENGTH: 41
<212> TYPE: DNA
<213> ORGANISM: Artificial Sequence
<220> FEATURE:
<223> OTHER INFORMATION: Bacteria
      synthesized oligonucleotide modified with label
```

<400> SEQUENCE: 1
gcgagtgcta aaccacatgc tccaccgctt gtggcactcg c                41

<210> SEQ ID NO 2
<211> LENGTH: 22
<212> TYPE: DNA
<213> ORGANISM: Artificial Sequence
<220> FEATURE:
<223> OTHER INFORMATION: Bacteria
      synthesized oligonucleotide modified with label

<400> SEQUENCE: 2
cgaattaaac cacatgctcc ac                                    22

<210> SEQ ID NO 3
<211> LENGTH: 24
<212> TYPE: DNA
<213> ORGANISM: Artificial Sequence
<220> FEATURE:
<223> OTHER INFORMATION: Bacteria
      synthesized oligonucleotide modified with label

<400> SEQUENCE: 3
gaccaggtaa ggttcttcgc gttg                                  24

<210> SEQ ID NO 4
<211> LENGTH: 64
<212> TYPE: DNA
<213> ORGANISM: Artificial Sequence
<220> FEATURE:
<223> OTHER INFORMATION: Viral/HIV
      Synthesized oligonucleotide; partially
      complementary to positions 911-974 of HIV-1 HXB2
      isolate.  Genbank accession M38432

<400> SEQUENCE: 4
gggacatcaa gcagccatgc aaatgttaaa agagaccatc aatgaggaag ctgcagaatg    60
ggat                                                                64

<210> SEQ ID NO 5
<211> LENGTH: 64
<212> TYPE: DNA
<213> ORGANISM: Artificial Sequence
<220> FEATURE:
<223> OTHER INFORMATION: Viral/HIV
      synthesized oligonucleotide; modified with
      acrydite

<400> SEQUENCE: 5
atcccattct gcagcttcct cattgatggt ctcttttaac atttgcatgg ctgcttgatg    60
tccc                                                                64

<210> SEQ ID NO 6
<211> LENGTH: 73
<212> TYPE: DNA
<213> ORGANISM: Artificial Sequence
<220> FEATURE:
<223> OTHER INFORMATION: Viral/HIV
      synthesized oligonucleotide

<400> SEQUENCE: 6
gagaccatca atgaggaagc tgcagaatgg gataatggag aaagacggag agcaatggag    60
aaagacggag agc                                                      73

<210> SEQ ID NO 7
<211> LENGTH: 60
<212> TYPE: DNA
<213> ORGANISM: Artificial Sequence
<220> FEATURE:
<223> OTHER INFORMATION: synthesized oligonucleotide

<400> SEQUENCE: 7
aatggagaaa gacggagagc caaaaacgat aaaccaacca caaaaacgat aaaccaacca        60

<210> SEQ ID NO 8
<211> LENGTH: 73
<212> TYPE: DNA
<213> ORGANISM: Artificial Sequence
<220> FEATURE:
<223> OTHER INFORMATION: synthesized oligonucleotide modified with
      acrydite

<400> SEQUENCE: 8
gctctccgtc tttctccatt gctctccgtc tttctccatt atcccattct gcagcttcct        60
cattgatggt ctc                                                          73

<210> SEQ ID NO 9
<211> LENGTH: 86
<212> TYPE: DNA
<213> ORGANISM: Artificial Sequence
<220> FEATURE:
<223> OTHER INFORMATION: synthesized oligonucleotide modified with label

<400> SEQUENCE: 9
caaaaacgat aaaccaacca gagaccatca atgaggaagc tgcagaatgg gatgagacca        60
tcaatgagga agctgcagaa tgggat                                            86

<210> SEQ ID NO 10
<211> LENGTH: 60
<212> TYPE: DNA
<213> ORGANISM: Artificial Sequence
<220> FEATURE:
<223> OTHER INFORMATION: synthiszed oligonucleotide - modified with
      acrydite

<400> SEQUENCE: 10
tggttggttt atcgttttg tggttggttt atcgttttg gctctccgtc tttctccatt          60

<210> SEQ ID NO 11
<211> LENGTH: 73
<212> TYPE: DNA
<213> ORGANISM: Artificial Sequence
<220> FEATURE:
<223> OTHER INFORMATION: synthesized oligonucleotide

<400> SEQUENCE: 11
gagaccatca atgaggaagc tgcagaatgg gataatggag aaagacggag agcaatggag        60
aaagacggag agc                                                          73

<210> SEQ ID NO 12
<211> LENGTH: 86
<212> TYPE: DNA
<213> ORGANISM: Artificial Sequence
<220> FEATURE:
<223> OTHER INFORMATION: synthesized oligonucleotide; modified with
      acrydite

<400> SEQUENCE: 12

-continued

```
atcccattct gcagcttcct cattgatggt ctcatcccat tctgcagctt cctcattgat      60
ggtctctggt tggtttatcg tttttg                                           86

<210> SEQ ID NO 13
<211> LENGTH: 35
<212> TYPE: DNA
<213> ORGANISM: Artificial Sequence
<220> FEATURE:
<223> OTHER INFORMATION: synthesized oligonucleotide; modified with
      acrydite

<400> SEQUENCE: 13
cctggtgcaa taggccctgc atgcactgga tgcac                                 35

<210> SEQ ID NO 14
<211> LENGTH: 29
<212> TYPE: DNA
<213> ORGANISM: Artificial Sequence
<220> FEATURE:
<223> OTHER INFORMATION: synthesized oligonucleotide primers for gag
      gene from HIV-1 from isolated HIV SF-2.  Genbank
      Accession number:  K02007

<400> SEQUENCE: 14
agttggagga catcaagcag catgcaaat                                        29

<210> SEQ ID NO 15
<211> LENGTH: 27
<212> TYPE: DNA
<213> ORGANISM: Artificial Sequence
<220> FEATURE:
<223> OTHER INFORMATION: synthesized oligonucleotide primers for gag
      gene from HIV-1 from isolated HIV SF-2 Gen Bank
      Accession No.  K02007

<400> SEQUENCE: 15
tgctatgtca gttccccttg gttctct                                          27
```